US012642545B2

(12) United States Patent
Hasenberg et al.

(10) Patent No.: US 12,642,545 B2
(45) Date of Patent: Jun. 2, 2026

(54) BURST MODE OPERATION OF INTRAVASCULAR LITHOTRIPSY (IVL)

(71) Applicant: Shockwave Medical, Inc., Santa Clara, CA (US)

(72) Inventors: Thomas Charles Hasenberg, Campbell, CA (US); Timothy Dominic Logsdon, Livermore, CA (US)

(73) Assignee: Shockwave Medical, Inc., Santa Clara, CA (US)

( * ) Notice: Subject to any disclaimer, the term of this patent is extended or adjusted under 35 U.S.C. 154(b) by 0 days.

(21) Appl. No.: 18/595,148

(22) Filed: Mar. 4, 2024

(65) Prior Publication Data

US 2025/0275782 A1     Sep. 4, 2025

(51) Int. Cl.
*A61B 17/22* (2006.01)

(52) U.S. Cl.
CPC ............... *A61B 17/22022* (2013.01); *A61B 2017/22008* (2013.01); *A61B 2017/22025* (2013.01)

(58) Field of Classification Search
CPC .... A61B 17/22; A61B 17/2202–22029; A61B 2017/22005–22091; A61B 2017/00137–00194
See application file for complete search history.

(56) References Cited

U.S. PATENT DOCUMENTS 2,916,647 A    12/1959  George
3,412,288 A    11/1968  Ostrander 3,413,976 A    12/1968  Roze
3,524,101 A    8/1970   Barbini
3,583,766 A    6/1971   Padberg
3,785,382 A    1/1974   Schmidt-Kloiber et al.
(Continued)

FOREIGN PATENT DOCUMENTS

AU    2009313507 B2    11/2014
AU    2013284490 B2    5/2018
(Continued)

OTHER PUBLICATIONS

International Search Report received for International Patent Application No. PCT/US2024/019721 mailed Nov. 22, 2024, 10 pages.

*Primary Examiner* — Elizabeth Houston
*Assistant Examiner* — Jonathan A Hollm
(74) *Attorney, Agent, or Firm* — Paradice & Li LLP

(57)                    ABSTRACT

Disclosed herein are systems and methods for applying voltage(s) across electrodes of a shock wave catheter system. The electrodes in the shock wave catheter may be activated by using at least one packet comprising a plurality of sub-pulses. The plurality of sub-pulses within a packet may be delivered in rapid succession (e.g., with a frequency of 100 Hz-10 kHz, pulse width duration of 1 μs or shorter, and/or peak power of 250 kW or higher). The packets may be delivered in bursts with, e.g., a frequency of 1-4 Hz). The time between adjacent sub-pulses may be less than the time between adjacent packets. The sub-pulses may be delivered with a higher peak power (lower energy) compared to non-burst pulses. The voltages of the sub-pulses may be applied using a single- or multi-stage generator circuit. The shock wave catheter may be operated in burst mode operation and/or non-burst mode operation.

19 Claims, 17 Drawing Sheets

(56) References Cited

U.S. PATENT DOCUMENTS

| | | | |
|---|---|---|---|
| 3,902,499 A * | 9/1975 | Shene | G10K 15/06 |
| | | | 606/128 |
| 3,942,531 A | 3/1976 | Hoff et al. | |
| 4,027,674 A * | 6/1977 | Tessler | A61B 17/22022 |
| | | | 606/128 |
| 4,030,505 A | 6/1977 | Tessler | |
| 4,191,189 A * | 3/1980 | Barkan | G10K 15/06 |
| | | | 606/128 |
| 4,445,509 A | 5/1984 | Auth | |
| 4,535,771 A * | 8/1985 | Takayama | G10K 15/06 |
| | | | 606/128 |
| 4,662,126 A | 5/1987 | Malcolm | |
| 4,662,375 A | 5/1987 | Hepp et al. | |
| 4,671,254 A | 6/1987 | Fair | |
| 4,685,458 A | 8/1987 | Leckrone | |
| 4,741,405 A | 5/1988 | Moeny et al. | |
| 4,809,682 A | 3/1989 | Forssmann et al. | |
| 4,813,934 A | 3/1989 | Engelson et al. | |
| 4,878,495 A | 11/1989 | Grayzei | |
| 4,890,603 A | 1/1990 | Filler | |
| 4,900,303 A | 2/1990 | Lemelson | |
| 4,990,134 A | 2/1991 | Auth | |
| 4,994,032 A | 2/1991 | Sugiyama et al. | |
| 5,009,232 A | 4/1991 | Hassler et al. | |
| 5,046,503 A | 9/1991 | Schneiderman | |
| 5,057,103 A | 10/1991 | Davis | |
| 5,057,106 A | 10/1991 | Kasevich et al. | |
| 5,061,240 A | 10/1991 | Cherian | |
| 5,078,717 A | 1/1992 | Parins et al. | |
| 5,102,402 A | 4/1992 | Dror et al. | |
| 5,103,804 A | 4/1992 | Abele et al. | |
| 5,116,227 A | 5/1992 | Levy | |
| 5,152,767 A | 10/1992 | Sypal et al. | |
| 5,152,768 A | 10/1992 | Bhatta | |
| 5,154,722 A | 10/1992 | Filip et al. | |
| 5,176,675 A | 1/1993 | Watson et al. | |
| 5,195,508 A | 3/1993 | Muller et al. | |
| 5,245,988 A | 9/1993 | Einars et al. | |
| 5,246,447 A | 9/1993 | Rosen et al. | |
| 5,254,121 A | 10/1993 | Manevitz et al. | |
| 5,281,231 A | 1/1994 | Rosen et al. | |
| 5,295,958 A | 3/1994 | Shturman | |
| 5,304,134 A | 4/1994 | Kraus et al. | |
| 5,321,715 A | 6/1994 | Trost | |
| 5,324,255 A | 6/1994 | Passafaro et al. | |
| 5,336,234 A | 8/1994 | Vigil et al. | |
| 5,362,309 A | 11/1994 | Carter | |
| 5,364,393 A | 11/1994 | Auth et al. | |
| 5,368,591 A | 11/1994 | Lennox et al. | |
| 5,395,335 A | 3/1995 | Jang | |
| 5,417,208 A | 5/1995 | Winkler | |
| 5,425,735 A | 6/1995 | Rosen et al. | |
| 5,454,809 A | 10/1995 | Janssen | |
| 5,472,406 A | 12/1995 | de la Torre et al. | |
| 5,582,578 A | 12/1996 | Zhong et al. | |
| 5,584,843 A | 12/1996 | Wulfman et al. | |
| 5,603,731 A | 2/1997 | Whitney | |
| 5,609,606 A | 3/1997 | O'Boyle | |
| 5,662,590 A | 9/1997 | de la Torre et al. | |
| 5,709,676 A | 1/1998 | Alt | |
| 5,846,218 A | 12/1998 | Brisken et al. | |
| 5,891,089 A | 4/1999 | Katz et al. | |
| 5,893,840 A | 4/1999 | Hull et al. | |
| 5,931,805 A | 8/1999 | Brisken | |
| 6,007,530 A | 12/1999 | Dornhofer et al. | |
| 6,033,371 A | 3/2000 | Torre et al. | |
| 6,056,722 A | 5/2000 | Jayaraman | |
| 6,080,119 A | 6/2000 | Schwarze et al. | |
| 6,083,232 A | 7/2000 | Cox | |
| 6,090,104 A | 7/2000 | Webster et al. | |
| 6,113,560 A | 9/2000 | Simnacher | |
| 6,132,444 A | 10/2000 | Shturman et al. | |
| 6,146,358 A | 11/2000 | Rowe | |
| 6,186,963 B1 | 2/2001 | Schwarze et al. | |
| 6,210,408 B1 | 4/2001 | Chandrasekaran et al. | |
| 6,215,734 B1 | 4/2001 | Moeny et al. | |
| 6,217,531 B1 | 4/2001 | Reitmajer | |
| 6,267,747 B1 | 7/2001 | Samson et al. | |
| 6,277,138 B1 | 8/2001 | Levinson et al. | |
| 6,287,272 B1 | 9/2001 | Brisken et al. | |
| 6,352,535 B1 | 3/2002 | Lewis et al. | |
| 6,364,894 B1 | 4/2002 | Healy et al. | |
| 6,367,203 B1 | 4/2002 | Graham et al. | |
| 6,371,971 B1 | 4/2002 | Tsugita et al. | |
| 6,398,792 B1 | 6/2002 | O'Connor | |
| 6,406,486 B1 | 6/2002 | de la Torre et al. | |
| 6,440,124 B1 | 8/2002 | Esch et al. | |
| 6,494,890 B1 | 12/2002 | Shturman et al. | |
| 6,514,203 B2 | 2/2003 | Bukshpan | |
| 6,524,251 B2 | 2/2003 | Rabiner et al. | |
| 6,589,253 B1 | 7/2003 | Cornish et al. | |
| 6,607,003 B1 | 8/2003 | Wilson | |
| 6,638,246 B1 | 10/2003 | Naimark et al. | |
| 6,652,547 B2 | 11/2003 | Rabiner et al. | |
| 6,666,834 B2 | 12/2003 | Restle et al. | |
| 6,689,089 B1 | 2/2004 | Tiedtke et al. | |
| 6,736,784 B1 | 5/2004 | Menne et al. | |
| 6,740,081 B2 | 5/2004 | Hilal | |
| 6,755,821 B1 | 6/2004 | Fry | |
| 6,939,320 B2 | 9/2005 | Lennox | |
| 6,989,009 B2 | 1/2006 | Lafontaine | |
| 7,066,904 B2 | 6/2006 | Rosenthal et al. | |
| 7,087,061 B2 | 8/2006 | Chernenko et al. | |
| 7,241,295 B2 | 7/2007 | Maguire | |
| 7,309,324 B2 | 12/2007 | Hayes et al. | |
| 7,389,148 B1 | 6/2008 | Morgan | |
| 7,505,812 B1 | 3/2009 | Eggers et al. | |
| 7,569,032 B2 | 8/2009 | Naimark et al. | |
| 7,850,685 B2 | 12/2010 | Kunis et al. | |
| 7,853,332 B2 | 12/2010 | Olsen et al. | |
| 7,873,404 B1 | 1/2011 | Patton | |
| 7,951,111 B2 | 5/2011 | Drasler et al. | |
| 8,162,859 B2 | 4/2012 | Schultheiss et al. | |
| 8,177,801 B2 | 5/2012 | Kallok et al. | |
| 8,353,923 B2 | 1/2013 | Shturman | |
| 8,556,813 B2 | 10/2013 | Cioanta et al. | |
| 8,574,247 B2 | 11/2013 | Adams et al. | |
| 8,728,091 B2 | 5/2014 | Hakala et al. | |
| 8,747,416 B2 | 6/2014 | Hakala et al. | |
| 8,888,788 B2 | 11/2014 | Hakala et al. | |
| 8,956,371 B2 | 2/2015 | Hawkins et al. | |
| 8,956,374 B2 | 2/2015 | Hawkins et al. | |
| 9,005,216 B2 | 4/2015 | Hakala et al. | |
| 9,011,462 B2 | 4/2015 | Adams et al. | |
| 9,011,463 B2 | 4/2015 | Adams et al. | |
| 9,044,618 B2 | 6/2015 | Hawkins et al. | |
| 9,044,619 B2 | 6/2015 | Hawkins et al. | |
| 9,072,534 B2 | 7/2015 | Hakala et al. | |
| 9,138,249 B2 | 9/2015 | Adams et al. | |
| 9,198,825 B2 | 12/2015 | Katragadda et al. | |
| 9,333,000 B2 | 5/2016 | Hakala et al. | |
| 9,421,025 B2 | 8/2016 | Hawkins et al. | |
| 9,433,428 B2 | 9/2016 | Hakala et al. | |
| 9,522,012 B2 | 12/2016 | Adams | |
| 9,642,673 B2 | 5/2017 | Adams et al. | |
| 9,993,292 B2 | 6/2018 | Adams et al. | |
| 10,039,561 B2 | 8/2018 | Adams et al. | |
| 10,118,015 B2 | 11/2018 | De La Rama et al. | |
| 10,149,690 B2 | 12/2018 | Hawkins et al. | |
| 10,154,799 B2 | 12/2018 | Van Der Weide et al. | |
| 10,159,505 B2 | 12/2018 | Hakala et al. | |
| 10,206,698 B2 | 2/2019 | Hakala et al. | |
| 10,226,265 B2 | 3/2019 | Ku et al. | |
| 10,517,620 B2 | 12/2019 | Adams | |
| 10,517,621 B1 | 12/2019 | Adams | |
| 10,555,744 B2 | 2/2020 | Nguyen et al. | |
| 10,682,178 B2 | 6/2020 | Adams et al. | |
| 10,702,293 B2 | 7/2020 | Hawkins et al. | |
| 10,709,462 B2 | 7/2020 | Nguyen et al. | |
| 10,959,743 B2 | 3/2021 | Adams et al. | |
| 10,966,737 B2 | 4/2021 | Nguyen | |
| 10,973,538 B2 | 4/2021 | Hakala et al. | |
| 11,000,299 B2 | 5/2021 | Hawkins et al. | |
| 11,076,874 B2 | 8/2021 | Hakala et al. | |

(56) References Cited

U.S. PATENT DOCUMENTS

| | | | |
|---|---|---|---|
| 11,337,713 | B2 | 5/2022 | Nguyen et al. |
| 11,432,834 | B2 | 9/2022 | Adams |
| 11,478,261 | B2 | 10/2022 | Nguyen |
| 11,534,187 | B2 | 12/2022 | Bonutti |
| 11,596,423 | B2 | 3/2023 | Nguyen et al. |
| 11,596,424 | B2 | 3/2023 | Hakala et al. |
| 11,622,780 | B2 | 4/2023 | Nguyen et al. |
| 11,696,799 | B2 | 7/2023 | Adams et al. |
| 11,771,449 | B2 | 10/2023 | Adams et al. |
| 2001/0037106 | A1* | 11/2001 | Shadduck .......... A61B 18/1492 |
| | | | 606/41 |
| 2001/0044596 | A1 | 11/2001 | Jaafar |
| 2002/0045890 | A1 | 4/2002 | Celliers et al. |
| 2002/0082553 | A1 | 6/2002 | Duchamp |
| 2002/0177889 | A1 | 11/2002 | Brisken et al. |
| 2003/0004434 | A1 | 1/2003 | Greco et al. |
| 2003/0176873 | A1 | 9/2003 | Chernenko et al. |
| 2003/0229370 | A1 | 12/2003 | Miller |
| 2004/0006333 | A1 | 1/2004 | Arnold et al. |
| 2004/0010249 | A1 | 1/2004 | Truckai et al. |
| 2004/0044308 | A1 | 3/2004 | Naimark et al. |
| 2004/0097963 | A1 | 5/2004 | Seddon |
| 2004/0097996 | A1 | 5/2004 | Rabiner et al. |
| 2004/0162508 | A1 | 8/2004 | Uebelacker |
| 2004/0249401 | A1 | 12/2004 | Rabiner et al. |
| 2004/0254570 | A1 | 12/2004 | Hadjicostis et al. |
| 2005/0015953 | A1 | 1/2005 | Keidar |
| 2005/0021013 | A1 | 1/2005 | Visuri et al. |
| 2005/0059965 | A1 | 3/2005 | Eberl et al. |
| 2005/0075662 | A1 | 4/2005 | Pedersen et al. |
| 2005/0090888 | A1 | 4/2005 | Hines et al. |
| 2005/0113722 | A1 | 5/2005 | Schultheiss |
| 2005/0113822 | A1 | 5/2005 | Fuimaono et al. |
| 2005/0171527 | A1 | 8/2005 | Bhola |
| 2005/0228372 | A1 | 10/2005 | Truckai et al. |
| 2005/0245866 | A1 | 11/2005 | Azizi |
| 2005/0251131 | A1 | 11/2005 | Lesh |
| 2006/0004286 | A1 | 1/2006 | Chang et al. |
| 2006/0069424 | A1 | 3/2006 | Acosta et al. |
| 2006/0074484 | A1 | 4/2006 | Huber |
| 2006/0184076 | A1 | 8/2006 | Gill et al. |
| 2006/0190022 | A1 | 8/2006 | Beyar et al. |
| 2006/0221528 | A1 | 10/2006 | Li et al. |
| 2007/0016112 | A1 | 1/2007 | Schultheiss et al. |
| 2007/0088380 | A1 | 4/2007 | Hirszowicz et al. |
| 2007/0129667 | A1 | 6/2007 | Tiedtke et al. |
| 2007/0156129 | A1 | 7/2007 | Kovalcheck |
| 2007/0239082 | A1 | 10/2007 | Schultheiss et al. |
| 2007/0239253 | A1 | 10/2007 | Jagger et al. |
| 2007/0244423 | A1 | 10/2007 | Zumeris et al. |
| 2007/0250052 | A1 | 10/2007 | Wham |
| 2007/0255270 | A1 | 11/2007 | Carney |
| 2007/0282301 | A1 | 12/2007 | Segalescu et al. |
| 2007/0299481 | A1 | 12/2007 | Syed et al. |
| 2008/0097251 | A1 | 4/2008 | Babaev |
| 2008/0188913 | A1 | 8/2008 | Stone et al. |
| 2009/0041833 | A1 | 2/2009 | Bettinger et al. |
| 2009/0227992 | A1 | 9/2009 | Nir et al. |
| 2009/0230822 | A1 | 9/2009 | Kushculey et al. |
| 2009/0247945 | A1 | 10/2009 | Levit et al. |
| 2009/0254114 | A1 | 10/2009 | Hirszowicz et al. |
| 2009/0299447 | A1 | 12/2009 | Jensen et al. |
| 2010/0016862 | A1 | 1/2010 | Hawkins et al. |
| 2010/0036294 | A1 | 2/2010 | Mantell et al. |
| 2010/0094209 | A1 | 4/2010 | Drasler et al. |
| 2010/0114020 | A1 | 5/2010 | Hawkins et al. |
| 2010/0114065 | A1 | 5/2010 | Hawkins et al. |
| 2010/0121322 | A1 | 5/2010 | Swanson |
| 2010/0179424 | A1 | 7/2010 | Warnking et al. |
| 2010/0286709 | A1 | 11/2010 | Diamant et al. |
| 2010/0305565 | A1 | 12/2010 | Truckai et al. |
| 2011/0034832 | A1 | 2/2011 | Cioanta et al. |
| 2011/0118634 | A1 | 5/2011 | Golan |
| 2011/0208185 | A1 | 8/2011 | Diamant et al. |
| 2011/0257523 | A1 | 10/2011 | Hastings et al. |
| 2011/0295227 | A1 | 12/2011 | Hawkins et al. |
| 2012/0071889 | A1 | 3/2012 | Mantell et al. |
| 2012/0095461 | A1 | 4/2012 | Herscher et al. |
| 2012/0116289 | A1 | 5/2012 | Hawkins et al. |
| 2012/0143177 | A1 | 6/2012 | Avitall et al. |
| 2012/0157991 | A1 | 6/2012 | Christian |
| 2012/0203255 | A1 | 8/2012 | Hawkins et al. |
| 2012/0253358 | A1 | 10/2012 | Golan et al. |
| 2013/0030431 | A1 | 1/2013 | Adams |
| 2013/0041355 | A1 | 2/2013 | Heeren et al. |
| 2013/0116714 | A1 | 5/2013 | Adams et al. |
| 2013/0123694 | A1 | 5/2013 | Subramaniyan et al. |
| 2013/0150874 | A1 | 6/2013 | Kassab |
| 2013/0253622 | A1 | 9/2013 | Hooven |
| 2014/0046229 | A1 | 2/2014 | Hawkins et al. |
| 2014/0052145 | A1 | 2/2014 | Adams et al. |
| 2014/0214061 | A1 | 7/2014 | Adams et al. |
| 2015/0320432 | A1* | 11/2015 | Adams ............ A61B 17/22012 |
| | | | 606/128 |
| 2016/0151081 | A1 | 6/2016 | Adams et al. |
| 2016/0324534 | A1 | 11/2016 | Hawkins et al. |
| 2017/0072225 | A1* | 3/2017 | Maxwell ................. A61N 7/00 |
| 2017/0135709 | A1 | 5/2017 | Nguyen et al. |
| 2017/0311965 | A1 | 11/2017 | Adams |
| 2019/0262594 | A1* | 8/2019 | Ogata ................... A61B 17/22 |
| 2021/0085383 | A1 | 3/2021 | Vo et al. |
| 2021/0338258 | A1 | 11/2021 | Hawkins et al. |
| 2022/0015785 | A1 | 1/2022 | Hakala et al. |
| 2022/0240958 | A1 | 8/2022 | Nguyen et al. |
| 2023/0043475 | A1 | 2/2023 | Adams |
| 2023/0107690 | A1 | 4/2023 | Nguyen |
| 2023/0165598 | A1 | 6/2023 | Nguyen et al. |
| 2023/0293197 | A1 | 9/2023 | Nguyen et al. |
| 2023/0310073 | A1 | 10/2023 | Adams et al. |
| 2023/0329731 | A1 | 10/2023 | Hakala et al. |
| 2023/0380849 | A1 | 11/2023 | Adams et al. |

FOREIGN PATENT DOCUMENTS

| | | | |
|---|---|---|---|
| CA | 2104414 | A1 | 2/1995 |
| CN | 1204242 | A | 1/1999 |
| CN | 1269708 | A | 10/2000 |
| CN | 1942145 | A | 4/2007 |
| CN | 101043914 | A | 9/2007 |
| CN | 102057422 | A | 5/2011 |
| CN | 102271748 | A | 12/2011 |
| CN | 102355856 | A | 2/2012 |
| CN | 102765785 | A | 11/2012 |
| CN | 203564304 | U | 4/2014 |
| CN | 115778485 | A | 3/2023 |
| CN | 115804628 | B | 3/2023 |
| CN | 117598753 | A | 2/2024 |
| DE | 3038445 | A1 | 5/1982 |
| DE | 202006014285 | U1 | 12/2006 |
| EP | 0442199 | A2 | 8/1991 |
| EP | 0460536 | A1 | 12/1991 |
| EP | 0571306 | A1 | 11/1993 |
| EP | 623360 | A1 | 11/1994 |
| EP | 0647435 | A1 | 4/1995 |
| EP | 2253884 | A1 | 11/2010 |
| EP | 2362798 | B1 | 4/2014 |
| JP | S62-099210 | U | 6/1987 |
| JP | S62-275446 | A | 11/1987 |
| JP | H03-63059 | A | 3/1991 |
| JP | H06-125915 | A | 5/1994 |
| JP | H07-47135 | A | 2/1995 |
| JP | H08-89511 | A | 4/1996 |
| JP | H10-99444 | A | 4/1998 |
| JP | H10-314177 | A | 12/1998 |
| JP | H10-513379 | A | 12/1998 |
| JP | 2002538932 | A | 11/2002 |
| JP | 2004081374 | A | 3/2004 |
| JP | 2004357792 | A | 12/2004 |
| JP | 2005501597 | A | 1/2005 |
| JP | 2005095410 | A | 4/2005 |
| JP | 2005515825 | A | 6/2005 |
| JP | 2006516465 | A | 7/2006 |
| JP | 2007289707 | A | 11/2007 |
| JP | 2007532182 | A | 11/2007 |

(56)                References Cited

FOREIGN PATENT DOCUMENTS

| | | | |
|---|---|---|---|
| JP | 2008506447 | A | 3/2008 |
| JP | 2011513694 | A | 4/2011 |
| JP | 2011520248 | A | 7/2011 |
| JP | 2011524203 | A | 9/2011 |
| JP | 2011528963 | A | 12/2011 |
| JP | 2012505050 | A | 3/2012 |
| JP | 2012508042 | A | 4/2012 |
| JP | 2015525657 | A | 9/2015 |
| JP | 2015528327 | A | 9/2015 |
| JP | 6029828 | B2 | 11/2016 |
| JP | 6081510 | B2 | 2/2017 |
| WO | WO-1989011307 | A1 | 11/1989 |
| WO | WO-1996024297 | A1 | 8/1996 |
| WO | WO-1999000060 | A1 | 1/1999 |
| WO | WO-1999002096 | A1 | 1/1999 |
| WO | WO-2000056237 | A2 | 9/2000 |
| WO | WO-2004069072 | A2 | 8/2004 |
| WO | WO-2005099594 | A1 | 10/2005 |
| WO | WO-2005102199 | A1 | 11/2005 |
| WO | WO-2006006169 | A2 | 1/2006 |
| WO | WO-2006127158 | A2 | 11/2006 |
| WO | WO-2007088546 | A2 | 8/2007 |
| WO | WO-2007149905 | A2 | 12/2007 |
| WO | WO-2009121017 | A1 | 10/2009 |
| WO | WO-2009126544 | A1 | 10/2009 |
| WO | WO-2009136268 | A1 | 11/2009 |
| WO | WO-2009152352 | A2 | 12/2009 |
| WO | WO-2010014515 | A2 | 2/2010 |
| WO | WO-2010054048 | A2 | 9/2010 |
| WO | WO-2011006017 | A1 | 1/2011 |
| WO | WO-2011094111 | A2 | 8/2011 |
| WO | WO-2011143468 | A2 | 11/2011 |
| WO | WO-2012025833 | A2 | 3/2012 |
| WO | WO-2013059735 | A1 | 4/2013 |
| WO | WO-2014025397 | A1 | 2/2014 |
| WO | WO-2014025620 | A1 | 2/2014 |
| WO | WO-2015017499 | A1 | 2/2015 |
| WO | WO-2019099218 | A1 | 5/2019 |
| WO | WO-2023197367 | A1 | 10/2023 |

* cited by examiner

Blow-Up of a Pulse Packet
with 24 μPulses

702

704

Time

Voltage

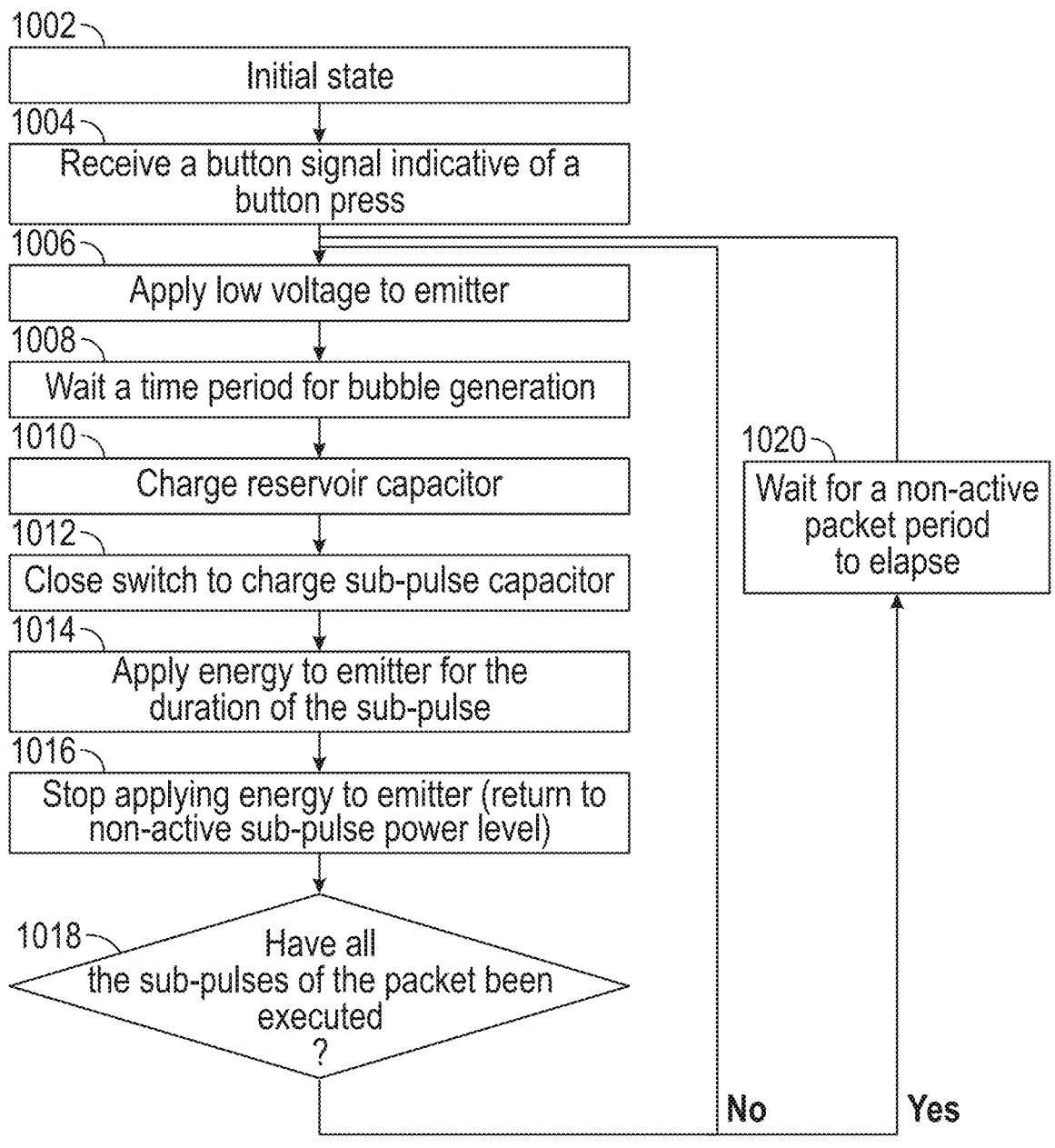

1002 — Initial state

1004 — Receive a button signal indicative of a button press

1006 — Apply low voltage to emitter

1008 — Wait a time period for bubble generation

1010 — Charge reservoir capacitor

1012 — Close switch to charge sub-pulse capacitor

1014 — Apply energy to emitter for the duration of the sub-pulse

1016 — Stop applying energy to emitter (return to non-active sub-pulse power level)

1018 — Have all the sub-pulses of the packet been executed?

1020 — Wait for a non-active packet period to elapse

No          Yes

FIG. 10

BURST MODE OPERATION OF INTRAVASCULAR LITHOTRIPSY (IVL)

FIELD OF THE DISCLOSURE

The present disclosure relates generally to the field of medical devices and methods, and more specifically to shock wave catheter devices for treating calcified lesions in body lumens, such as calcified lesions and occlusions in vasculature and kidney stones in the urinary system.

BACKGROUND

A wide variety of catheters have been developed for treating calcified lesions, such as calcified lesions in vasculature associated with arterial disease. For example, treatment systems for percutaneous coronary angioplasty or peripheral angioplasty use angioplasty balloons to dilate a calcified lesion and restore normal blood flow in a vessel. In these types of procedures, a catheter carrying a balloon is advanced into the vasculature along a guide wire until the balloon is aligned with calcified plaques. The balloon is then pressurized (normally to greater than 10 atm), causing the balloon to expand in a vessel to push calcified plaques back into the vessel wall and dilate occluded regions of vasculature.

More recently, the technique and treatment of intravascular lithotripsy (IVL) has been developed, which is an interventional procedure to modify calcified plaque in diseased arteries. The mechanism of plaque modification is through use of a catheter having one or more acoustic shock wave generating sources located within a liquid that can generate acoustic shock waves that modify the calcified plaque. IVL devices vary in design with respect to the energy source used to generate the acoustic shock waves, with two exemplary energy sources being electrohydraulic generation and laser generation.

For electrohydraulic generation of acoustic shock waves, a conductive solution (e.g., saline) may be contained within an enclosure that surrounds electrodes or can be flushed through a tube that surrounds the electrodes. The calcified plaque modification is achieved by creating acoustic shock waves within the catheter by an electrical discharge across the electrodes. The energy from this electrical discharge enters the surrounding fluid faster than the speed of sound, generating an acoustic shock wave. In addition, the energy creates one or more rapidly expanding and collapsing vapor bubbles that generate secondary shock waves. The shock waves propagate radially outward and modify calcified plaque within the blood vessels. For laser generation of acoustic shock waves, a laser pulse is transmitted into and absorbed by a fluid within the catheter. This absorption process rapidly heats and vaporizes the fluid, thereby generating the rapidly expanding and collapsing vapor bubble, as well as the acoustic shock waves that propagate outward and modify the calcified plaque. The acoustic shock wave intensity is higher if a fluid is chosen that exhibits strong absorption at the laser wavelength that is employed. These examples of IVL devices are not intended to be a comprehensive list of potential energy sources to create IVL shock waves.

The IVL process may be considered different from standard atherectomy procedures in that it cracks calcium but does not liberate the cracked calcium from the tissue. Hence, generally speaking, IVL should not require aspiration nor embolic protection. Further, due to the compliance of a normal blood vessel and non-calcified plaque, the shock waves produced by IVL do not modify the normal vessel tissue or non-calcified plaque. Moreover, IVL does not carry the same degree of risk of perforation, dissection, or other damage to vasculature as atherectomy procedures or angioplasty procedures using cutting or scoring balloons.

More specifically, catheters to deliver IVL therapy have been developed that include pairs of electrodes for electrohydraulically generating shock waves inside an angioplasty balloon. Shock wave devices can be particularly effective for treating calcified plaque lesions because the acoustic pressure from the shock waves can crack and disrupt lesions near the angioplasty balloon without harming the surrounding tissue. In these devices, the catheter is advanced over a guidewire through a patient's vasculature until it is positioned proximal to and/or aligned with a calcified plaque lesion in a body lumen. The balloon is then inflated with conductive fluid (using a relatively low pressure of 2-4 atm) so that the balloon expands to contact the lesion, but is not an inflation pressure that substantively displaces the lesion. Voltage pulses can then be applied across the electrodes of the electrode pairs to produce acoustic shock waves that propagate through the walls of the angioplasty balloon and into the lesions. Once the lesions have been cracked by the acoustic shock waves, the balloon can be expanded further to increase the cross-sectional area of the lumen and improve blood flow through the lumen. Alternative devices to deliver IVL therapy can be within a closed volume other than an angioplasty balloon, such as a cap, balloons of various compliances, or other enclosures.

The voltage pulses may be non-burst pulses applied across the electrodes of the electrode pairs and may be effective at producing the shock waves to treat, e.g., calcium lesions. A conductive solution (e.g., saline) may be contained within an enclosure that surrounds the electrodes or can be flushed through a tube that surrounds the electrodes. Acoustic shock waves may be created within the catheter by an electrical discharge across the electrodes. These shock waves propagate radially outward and modify calcified plaque. In some embodiments, laser generation of acoustic shock waves is used, where a laser pulse is transmitted into and absorbed by a fluid within the catheter. This absorption process rapidly heats and vaporizes the fluid, thereby generating the rapidly expanding vapor bubble, as well as the acoustic shock waves that propagate outward and modify the calcified plaque. More effective techniques for delivering shock wave therapy may be desirable.

SUMMARY

Described herein are systems and methods for applying one or more voltages across electrodes of a shock wave catheter system. The electrodes in the shock wave catheter may be activated by using at least one packet, which comprises a plurality of sub-pulses. The plurality of sub-pulses within a packet may be delivered in rapid succession (e.g., with a frequency of 100 Hz-10 kHz), and the packets may be delivered in bursts. In some embodiments, the time between adjacent sub-pulses may be less than the time between adjacent packets. The packets may have a frequency of 1-4 Hz, for example. Embodiments of the disclosures may comprise applying sub-pulses having a higher peak power (but lower energy) to the electrodes of the shock wave catheter system compared to non-burst pulses.

A method for generating one or more shock waves in a shock wave catheter system is disclosed. The method comprises: applying a first voltage to one or more electrodes of the shock wave catheter system to generate one or more bubbles in a fluid surrounding the one or more electrodes; and applying at least one packet of one or more second voltages to the one or more electrodes to generate one or more electrical arcs at the one or more electrodes, wherein: each of the at least one packet comprises a plurality of sub-pulses, and at least one of the plurality of sub-pulses has a duration of 1 μs or shorter, or a frequency of the plurality of sub-pulses is between 100 Hz to 10 KHz; wherein the one or more second voltages are different from the first voltage. Additionally or alternatively, in some embodiments, properties of the plurality of sub-pulses are based on properties of calcium and/or tissue treated by the shock wave catheter system, wherein the properties of the calcium and/or tissue comprise a hardness, thickness, acoustic properties, or a combination thereof. Additionally or alternatively, in some embodiments, the properties of the plurality of sub-pulses include a number of the plurality of sub-pulses within the at least one packet, a duration of the at least one sub-pulse, a peak power of the at least one sub-pulse, a frequency of the plurality of sub-pulses, an electrical pulse amplitude, a sonic output, or a combination thereof. Additionally or alternatively, in some embodiments, a number of the plurality of sub-pulses is greater than or equal to 10. Additionally or alternatively, in some embodiments, the at least one packet has a duration of 20 μs or longer, a duty cycle of 50%, or both. Additionally or alternatively, in some embodiments, a plurality of packets has a frequency between 1 to 4 Hz, wherein the plurality of packets includes the at least one packet. Additionally or alternatively, in some embodiments, a frequency of the plurality of sub-pulses is 100 times more than a frequency of a plurality of packets, wherein the plurality of packets includes the at least one packet. Additionally or alternatively, in some embodiments, the method further comprises: applying one or more third voltages during one or more non-active sub-pulse periods between the plurality of sub-pulses. Additionally or alternatively, in some embodiments, the one or more non-active sub-pulse periods have a power level that is 50% or less than a power level of the plurality of sub-pulses. Additionally or alternatively, in some embodiments, a peak power of the at least one sub-pulse is 250 kW or higher.

A shock wave catheter system is disclosed. The shock wave catheter system comprises: one or more electrodes; a fluid surrounding the one or more electrodes; a first voltage source configured to apply a first voltage to the one or more electrodes to generate one or more bubbles in the fluid; and a second voltage source configured to apply at least one packet of one or more second voltages to the one or more electrodes to generate one or more electrical arcs at the one or more electrodes, wherein the at least one packet comprises a plurality of sub-pulses, wherein at least one of the plurality of sub-pulses has a duration of 1 μs or shorter, or a frequency of the plurality of sub-pulses is between 100 Hz to 10 kHz. Additionally or alternatively, in some embodiments, the shock wave catheter system further comprises: a controller configured to control properties of the plurality of sub-pulses based on properties of calcium and/or tissues treated by the shock wave catheter system, wherein the properties of the calcium and/or tissue comprise a hardness, thickness, acoustic properties, or a combination thereof. Additionally or alternatively, in some embodiments, the properties of the plurality of sub-pulses include a number of the plurality of sub-pulses within the at least one packet, a duration of the at least one sub-pulse, a peak power of the at least one sub-pulse, an electrical pulse amplitude, a sonic output, or a combination thereof. Additionally or alternatively, in some embodiments, a number of the plurality of sub-pulses is greater than or equal to 10. Additionally or alternatively, in some embodiments, the at least one packet has a duration of 20 μs or longer, a duty cycle of 50%, or both. Additionally or alternatively, in some embodiments, a plurality of packets has a frequency between 1 to 4 Hz, wherein the plurality of packets includes the at least one packet. Additionally or alternatively, in some embodiments, the first voltage source is a low power voltage source, and the second voltage source is a high-power voltage source. Additionally or alternatively, in some embodiments, the one or more electrodes comprise an electrode pair separated by an electrode gap and the one or more second voltages are applied across the electrode gap.

A method for generating one or more shock waves in a shock wave catheter system is disclosed. The method comprises: applying a first voltage to one or more electrodes of the shock wave catheter system to generate one or more bubbles in a fluid surrounding the one or more electrodes; and applying a plurality of sub-pulses of one or more second voltages to the one or more electrodes to generate one or more electrical arcs at the one or more electrodes, wherein the plurality of sub-pulses has a frequency greater than 10 Hz.

A shock wave catheter system is disclosed. A shock wave catheter system comprises: one or more electrodes; a fluid surrounding the one or more electrodes; a first voltage source configured to apply a first voltage to the one or more electrodes to generate one or more bubbles in the fluid; and a second voltage source configured to apply a plurality of sub-pulses of one or more second voltages to the one or more electrodes to generate one or more electrical arcs at the one or more electrodes, wherein the plurality of sub-pulses has a frequency greater than 10 Hz.

A method for generating one or more shock waves in a shock wave catheter system is disclosed. The method comprises: applying a first voltage to one or more electrodes of the shock wave catheter system to generate one or more bubbles in a fluid surrounding the one or more electrodes; and applying a plurality of packets of one or more second voltages to the one or more electrodes to generate one or more electrical arcs at the one or more electrodes, wherein the plurality of packets has a frequency greater than 1 Hz, wherein applying the plurality of packets of the one or more second voltages comprises: for each of the plurality of packets, applying a plurality of sub-pulses of the one or more second voltages to the one or more electrodes.

A shock wave catheter system is disclosed. The shock wave catheter system comprises: one or more electrodes; a fluid surrounding the one or more electrodes; a first voltage source configured to apply a first voltage to the one or more electrodes to generate one or more bubbles in the fluid; and a second voltage source configured to apply a plurality of packets of one or more second voltages to the one or more electrodes to generate one or more electrical arcs at the one or more electrodes, wherein the plurality of packets has a frequency greater than 1 Hz, wherein the second voltage source applying the plurality of packets of the one or more second voltages comprises: for each of the plurality of packets, applying a plurality of sub-pulses of the one or more second voltages to the one or more electrodes.

A method for operating a shock wave catheter system is disclosed. The method comprises: applying a first voltage to one or more electrodes of the shock wave catheter system to generate one or more bubbles in a fluid surrounding the one or more electrodes; charging a reservoir capacitor using a second voltage source; charging a sub-pulse capacitor using the reservoir capacitor; and for a plurality of sub-pulses included in a packet, delivering energy stored in the sub-pulse capacitor to the one or more electrodes to generate one or more electrical arcs at the one or more electrodes.

A circuit is disclosed. The circuit comprises: a first voltage source configured to apply a first voltage to one or more electrodes of a shock wave catheter system to generate one or more bubbles in a fluid surrounding the one or more electrodes; a second voltage source configured to apply a second voltage; a reservoir capacitor coupled to the second voltage source and configured to store a charge from the second voltage source; and a sub-pulse capacitor coupled to the reservoir capacitor, wherein the sub-pulse capacitor is configured to store a charge from the reservoir capacitor and transfer stored energy to the one or more electrodes to generate one or more electrical arcs at the one or more electrodes.

A shock wave catheter system is disclosed. The shock wave catheter system comprises: one or more electrodes; a fluid surrounding the one or more electrodes; a first voltage source configured to apply a first voltage to the one or more electrodes to generate one or more bubbles in the fluid; a second voltage source configured to apply a second voltage; a reservoir capacitor coupled to the second voltage source and configured to store a charge from the second voltage source; and a sub-pulse capacitor coupled to the reservoir capacitor, wherein the sub-pulse capacitor is configured to store a charge from the reservoir capacitor and transfer stored energy to the one or more electrodes to generate one or more electrical arcs at the one or more electrodes.

A method for operating a shock wave catheter system is disclosed. The method comprises: applying a first voltage to one or more electrodes of the shock wave catheter system to generate one or more bubbles in a fluid surrounding the one or more electrodes; charging a capacitor using a second voltage source; and for a plurality of sub-pulses included in a packet, delivering energy stored in the capacitor to the one or more electrodes to generate one or more electrical arcs at the one or more electrodes, wherein at least one of the plurality of sub-pulses has a duration of 1 µs or shorter, or a frequency of the plurality of sub-pulses is between 100 Hz to 10 kHz.

A circuit is disclosed. The circuit comprises: a first voltage source configured to apply a first voltage to one or more electrodes of a shock wave catheter system to generate one or more bubbles in a fluid surrounding the one or more electrodes; a second voltage source configured to apply a second voltage comprising a plurality of sub-pulses; and a capacitor coupled to the second voltage source, wherein the capacitor is configured to store a charge from the second voltage source and transfer stored energy to the one or more electrodes to generate one or more electrical arcs at the one or more electrodes, wherein at least one of the plurality of sub-pulses has a duration of 1 µs or shorter, or a frequency of the plurality of sub-pulses is between 100 Hz to 10 kHz.

A shock wave catheter system is disclosed. The shock wave catheter system comprises: one or more electrodes; a fluid surrounding the one or more electrodes; a first voltage source configured to apply a first voltage to the one or more electrodes to generate one or more bubbles in the fluid; a second voltage source configured to apply a second voltage comprising a plurality of sub-pulses; a capacitor coupled to the second voltage source, wherein the capacitor is configured to store a charge from the second voltage source and transfer stored energy to the one or more electrodes to generate one or more electrical arcs at the one or more electrodes, wherein at least one of the plurality of sub-pulses has a duration of 1 µs or shorter, or a frequency of the plurality of sub-pulses is between 100 Hz to 10 KHz.

A method of treating a lesion in a body lumen is disclosed. The method comprises: advancing a shock wave catheter to the lesion through the body lumen; and applying a packet of voltage pulses, the packet comprising a plurality of sub-pulses delivered at a frequency of at least 10 Hz, wherein each of the plurality of sub-pulses generates a shock wave. Additionally or alternatively, in some embodiments, properties of the plurality of sub-pulses are based on properties of calcium and/or tissue treated by the shock wave catheter, wherein the properties of the calcium and/or tissue comprise a hardness, thickness, acoustic properties, or a combination thereof. Additionally or alternatively, in some embodiments, the properties of the plurality of sub-pulses include a number of the plurality of sub-pulses within the at least one packet, a duration of the at least one sub-pulse, a peak power of the at least one sub-pulse, a frequency of the plurality of sub-pulses, an electrical pulse amplitude, a sonic output, or a combination thereof. Additionally or alternatively, in some embodiments, a number of the plurality of sub-pulses is greater than or equal to 10. Additionally or alternatively, in some embodiments, the packet has a duration of 20 µs or longer, a duty cycle of 50%, or both. Additionally or alternatively, in some embodiments, a plurality of packets has a frequency between 1 to 4 Hz, wherein the plurality of packets includes the packet. Additionally or alternatively, in some embodiments, a frequency of the plurality of sub-pulses is 100 times more than a frequency of a plurality of packets, wherein the plurality of packets includes the packet. Additionally or alternatively, in some embodiments, the method further comprises: applying one or more second voltages during one or more non-active sub-pulse periods between the plurality of sub-pulses. Additionally or alternatively, in some embodiments, the one or more non-active sub-pulse periods have a power level that is 50% or less than a power level of the plurality of sub-pulses. Additionally or alternatively, in some embodiments, a peak power of at least one of the plurality of sub-pulses is 250 kW or higher.

A shock wave catheter system is disclosed. The shock wave catheter system comprises: one or more electrodes; a fluid surrounding the one or more electrodes; and one or more voltage sources configured to apply one or more voltages to the one or more electrodes in accordance with a mode of operation, wherein the mode of operation comprises a burst mode operation and a non-burst mode operation, wherein the burst mode operation comprises applying at least one packet of the one or more voltages to the one or more electrodes, each of the at least one packet comprises a plurality of sub-pulses, and at least one of the plurality of sub-pulses has a duration of 1 µs or shorter, or a frequency of the plurality of sub-pulses is between 100 Hz to 10 KHz.

A method for operating a shock wave catheter system is disclosed. A method for operating a shock wave catheter system, comprising: operating the shock wave catheter system in a burst mode operation, wherein the burst mode operation comprises applying at least one packet of one or more voltages to one or more electrodes of the shock wave catheter system, wherein: each of the at least one packet comprises a plurality of sub-pulses, and at least one of the plurality of sub-pulses has a duration of 1 µs or shorter, or a frequency of the plurality of sub-pulses is between 100 Hz to 10 kHz; and operating the shock wave catheter system in a non-burst mode operation.

DESCRIPTION OF THE FIGURES

The invention will now be described, by way of example only, with reference to the accompanying drawings, in which:

FIG. 10 illustrates an exemplary flow chart for burst mode operation of an IVL catheter, according to some embodiments.

DETAILED DESCRIPTION

Figure 1:
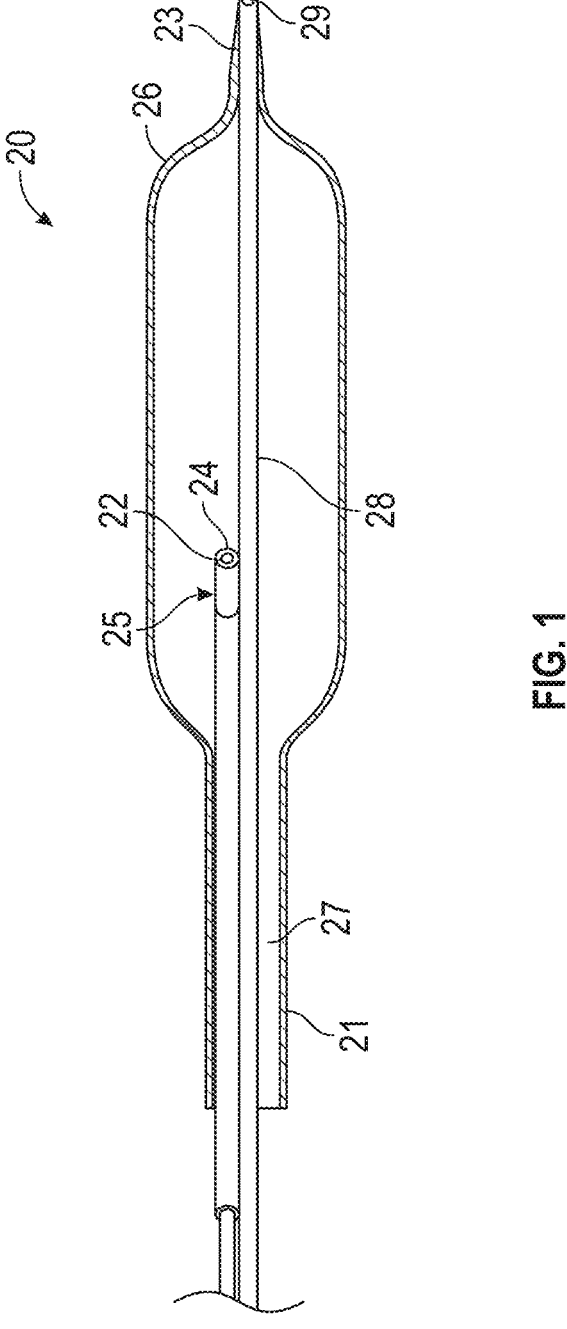
FIG. 1 illustrates a side view of an exemplary angioplasty balloon catheter, according to some embodiments.

The following description is presented to enable a person of ordinary skill in the art to make and use the various embodiments and aspects thereof disclosed herein. Descriptions of specific devices, assemblies, techniques, and applications are provided only as examples. Various modifications to the examples described herein will be readily apparent to those of ordinary skill in the art, and the general principles described herein may be applied to other examples and applications without departing from the spirit and scope of the various embodiments and aspects thereof. Thus, the various embodiments and aspects thereof are not intended to be limited to the examples described herein and shown but are to be accorded the scope consistent with the claims.

Efforts have been made to improve the design of electrode assemblies included in shock wave and directed cavitation catheters. For instance, low-profile electrode assemblies have been developed that reduce the crossing profile of a catheter and allow the catheter to more easily navigate calcified vessels to deliver shock waves in more severely occluded regions of vasculature. Examples of low-profile electrode designs can be found in U.S. Pat. Nos. 8,888,788, 9,433,428, and 10,709,462, and in U.S. Publication No. 2021/0085383, all of which are incorporated herein by reference. Other catheter designs have improved the delivery of shock waves, for instance, by specific electrode construction and configuration thereby directing shock waves in a forward direction to break up tighter and harder-to-cross occlusions in vasculature. Examples of forward-firing catheter designs can be found in U.S. Pat. Nos. 10,966,737, 11,478,261, and 11,596,423 and U.S. Publication Nos. 2023/0107690 and 2023/0165598, all of which are incorporated herein by reference. Efforts to improve the longevity of electrode assemblies have included switching or alternating the polarity of the voltage source. Examples of polarity switching in a shock wave device can be found in U.S. Pat. No. 10,226,265, which is incorporated herein by reference.

In the following description of the various embodiments, reference is made to the accompanying drawings, in which are shown, by way of illustration, specific embodiments that can be practiced. It is to be understood that other embodiments and examples can be practiced, and changes can be made without departing from the scope of the disclosure.

In addition, it is also to be understood that the singular forms "a," "an," and "the" used in the following description are intended to include the plural forms as well, unless the context clearly indicates otherwise. It is also to be understood that the term "and/or" as used herein refers to and encompasses any and all possible combinations of one or more of the associated listed items. It is further to be understood that the terms "includes, "including," "comprises," and/or "comprising," when used herein, specify the presence of stated features, integers, steps, operations, elements, components, and/or units but do not preclude the presence or addition of one or more other features, integers, steps, operations, elements, components, units, and/or groups thereof. As provided herein, it should be appreciated that any disclosure of a numerical range describing dimensions or measurements such as thicknesses, length, weight, time, frequency, temperature, voltage, current, angle, etc. is inclusive of any numerical increment or gradient within the ranges set forth relative to the given dimension or measurement.

FIG. 1 illustrates a side view of an exemplary angioplasty balloon catheter, according to some embodiments. Catheter 20 includes an elongated carrier such as a hollow sheath 21, a dilating balloon 26 formed about a sheath 21 in sealed relation thereto, and a guide wire member 28 to which the balloon 26 is scaled at a seal 23. The guide wire member 28 may have a longitudinal lumen 29 through which a guide wire (not shown) may be received for directing the catheter 20 to a desired location within a vein or artery, for example.

The sheath 21 forms, with the guide wire member 28, a channel 27 through which fluid may be admitted into the balloon 26 to inflate the balloon. The balloon 26 may be filled with water, saline, a mixed saline solution, etc., allowing the balloon to be gently placed along the walls of the artery or vein, for example, in direct proximity with the calcified lesion. The fluid may also contain an x-ray contrast to permit fluoroscopic viewing of the catheter during use.

The channel 27 is in fluid communication with an electrode pair 25 and provides the conductive fluid necessary for current to flow across an electrode gap of the electrode pair 25 and subsequent shock wave generation. The electrode pair 25 may include electrodes 22 and 24 within the fluid filled balloon 26.

Although FIG. 1 illustrates and the corresponding descriptions are specific to an intravascular lithotripsy (IVL) angioplasty balloon catheter, embodiments of the disclosure are applicable to other types of IVL, where a balloon may or may not be used. Additionally or alternatively, embodiments of the disclosure may include a plurality of electrode pairs 25.

In some embodiments, an IVL catheter is a so-called "rapid exchange-type" ("Rx") catheter provided with an opening portion through which a guide wire is guided (e.g., through a middle portion of a central tube in a longitudinal direction). In other embodiments, an IVL catheter may be an "over-the-wire-type" ("OTW") catheter in which a guide wire lumen is formed throughout the overall length of the catheter, and a guide wire is guided through the proximal end of a hub.

Figures 2, 3:
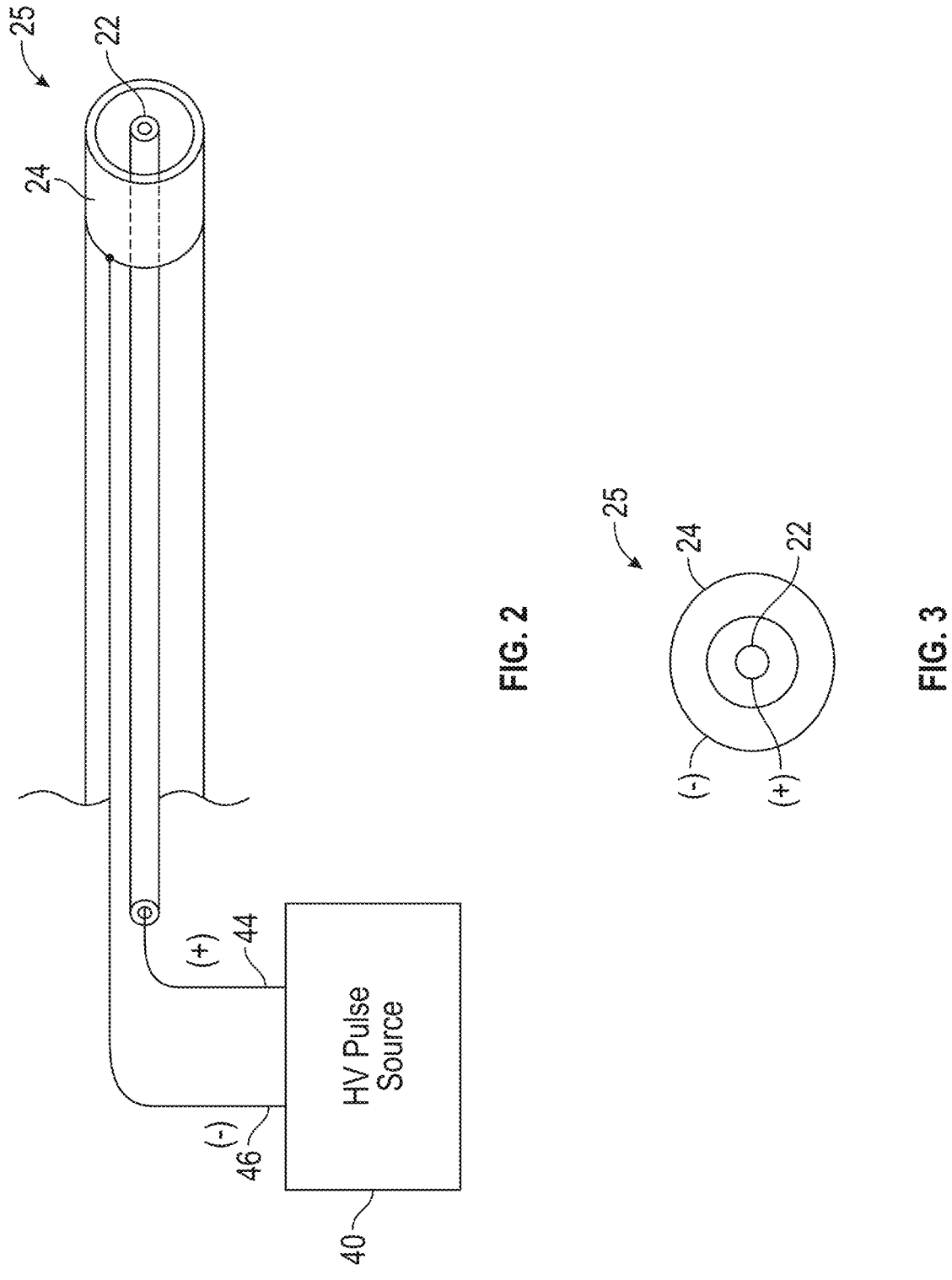
FIG. 2 illustrates a side view of example electrodes electrically coupled to a voltage source, according to some embodiments.
FIG. 3 illustrates example inner and outer electrodes, according to some embodiments.

As shown in FIG. 2, the electrodes 22 and 24 may be electrically coupled to a source 40 (e.g., a voltage source). The electrodes 22 and 24 may be electrically coupled to the source 40 through a connector, for example. In some embodiments, the source 40 may be a high voltage power supply (HVPS). The source 40 may apply one or more voltages to the electrode 22, the electrode 24, or both to generate one or more electrical arcs at the electrodes.

As may be seen in FIG. 3, the electrodes 22 and 24 are coaxially disposed with electrode 22 being an inner electrode and electrode 24 being an outer electrode. Referring back to FIG. 2, the inner electrode 22 may be coupled to a positive terminal 44 of the source 40, and the outer electrode 24 may be coupled to a negative terminal 46 of the source 40. In some aspects, the system may employ polarity switching, where the inner electrode 22 may be coupled to the negative terminal 46 of the source 40, and the outer electrode 24 may be coupled to the positive terminal 44 of the source 40. The electrodes 22 and 24 may be formed of metal, such as stainless steel, or another conductive material. The electrodes 22 and 24 may be spatially separated by a certain distance to allow a reproducible arc to form for a given applied voltage and current.

The electrical arcs between electrodes 22 and 24 in the fluid are used to generate shock waves in the fluid (within channel 27). A pulse of high voltage applied to the electrodes 22 and 24 may form an arc across the electrodes 22 and 24. Once the catheter 20 is positioned at a lesion site with the guide wire (not shown), the physician or operator can start applying pulses to the electrodes 22 and 24 (e.g., by pressing a button that controls the catheter system) to form the shock waves that crack the calcified plaque. Such shock waves may propagate through the fluid, through the balloon 26, through the blood and vessel wall to the calcified lesion where the energy may break the hardened plaque without the application of excessive pressure by the balloon on the walls of the artery.

The device 200 may include multiple electrode pairs along the length of the balloon 26. A shock wave device having multiple shock wave electrode pairs at different locations (circumferentially and/or longitudinally) may help to provide consistent or uniform force to a region of tissue. The electrode pairs may be electrically coupled in series or in parallel.

As used herein, the term "electrode" refers to an electrically conducting element (typically made of metal) that receives electrical current and subsequently releases the electrical current to another electrically conducting element. In the context of the present disclosure, electrodes are often positioned relative to each other, such as in an arrangement of an inner electrode and an outer electrode. Accordingly, as used herein, the term "electrode pair" refers to two electrodes that are positioned adjacent to and spaced apart from each other such that application of a sufficiently high voltage to the electrode pair will cause an electrical current to transmit across the gap (also referred to as a "spark gap") between the two electrodes (e.g., from an inner electrode to an outer electrode, or vice versa, optionally with the electricity passing through a conductive fluid or gas therebetween). In some contexts, one or more electrode pairs may also be referred to as an electrode assembly. In the context of the present disclosure, the term "emitter" broadly refers to the region of an electrode assembly where the current transmits across the electrode pair, generating a shock wave. The terms "emitter sheath" and "emitter band" refer to a continuous or discontinuous band of conductive material that may form one or more electrodes of one or more electrode pairs, thereby forming a location of one or more emitters.

Figure 4:
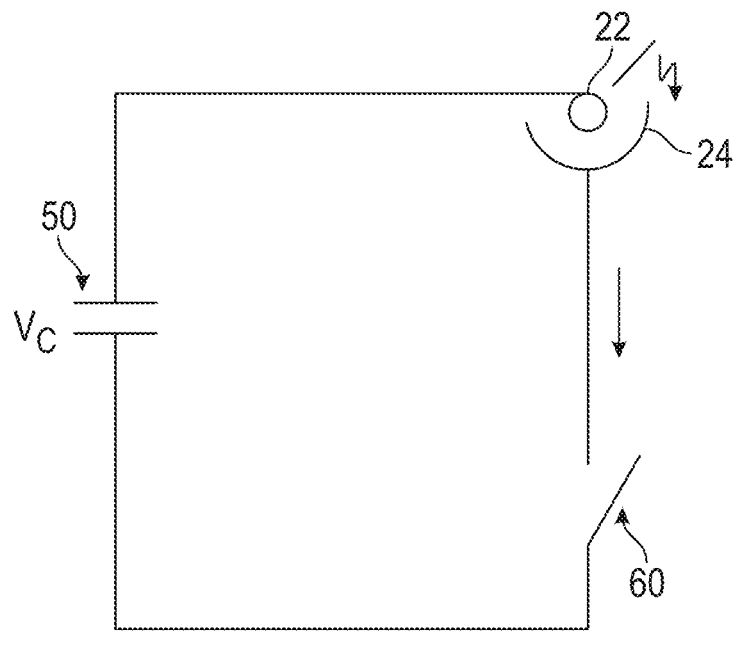
FIG. 4 illustrates an exemplary simplified equivalent circuit diagram, according to some embodiments.

FIG. 4 illustrates an exemplary simplified equivalent circuit diagram, according to some embodiments. The circuit may include a capacitor 50 that stores a voltage Vc. A switch 60 may be closed, allowing a voltage drop across the electrodes 22 and 24.

Figure 5:
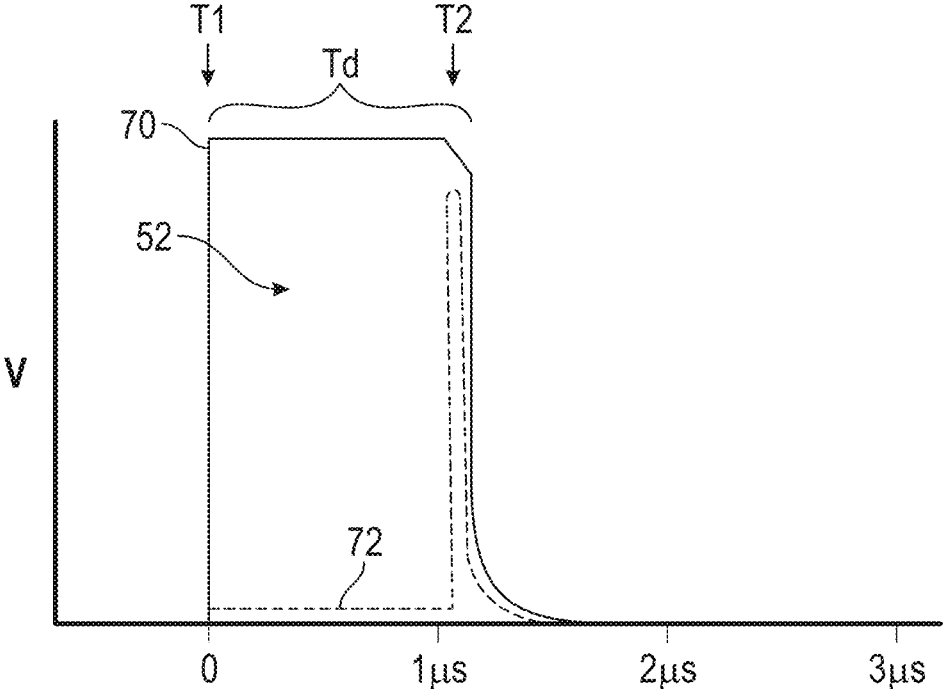
FIG. 5 illustrates an exemplary graph of a pulse applied to the electrodes and the resulting current flow through the electrodes, according to some embodiments.

FIG. 5 illustrates an exemplary graph of a pulse applied to the electrodes 22 and 24 and the resulting current flow through the electrodes 22 and 24, according to some embodiments. The switch 60 may be first closed at time T1. At time T1, the voltage is low, and closing the switch 60 causes the voltage across the electrodes 22 and 24 to quickly rise to a voltage level 70. During this time, the current 72 through the electrodes 22 and 24 is relatively low. After a dwell time Td, when the voltage across the electrodes 22 and 24 reaches the breakdown voltage of the liquid between the electrodes 22 and 24, an electrical arc occurs across the electrodes 22 and 24. After the dwell time Td, at time T2, the electrical arc causes a high current 72 to begin to flow through the electrodes 22 and 24 and a plasma to form between the electrodes 22 and 24. The plasma rapidly heats the liquid and creates a shock wave because the energy is transferred to the liquid faster than the speed of sound. In addition, the energy transfer to the liquid rapidly heats and vaporizes fluid thereby forming a vapor bubble. The bubble expands and then is cooled by the denser surrounding liquid and ultimately collapses. If the bubble is allowed to grow unimpeded to its equilibrium size, then the collapse may result in a second acoustic pulse as well as the emission of a water jet. This water jet results from the walls of the dense liquid colliding when the bubble collapses completely.

In some instances, calcium lesions may require high pressures (sometimes as high as 10-15 or even 20 atm) to break up the calcified plaque and push it back into the vessel wall. The system includes a pulse generator that is coupled to the proximal ends of insulated wires that provide one or more voltages to the shock wave generator. As a voltage is applied across an electrode pair by the pulse generator, each pulse initially ionizes the conductive fluid inside the balloon 26 to generate small gas bubbles around the shock wave generators that insulate the electrodes. Subsequently, a plasma arc forms across a gap between the electrodes of the electrode pairs, generating a low impedance path where current flows freely. The heat from the plasma arc heats the conductive fluid to generate a rapidly expanding vapor bubble. The expansion and collapse of the vapor bubble generates a shock wave (cavitation wave) that radiates outwardly through the balloon 26 and then through the blood to the calcified lesion proximate to the balloon 26.

Figure 6A:
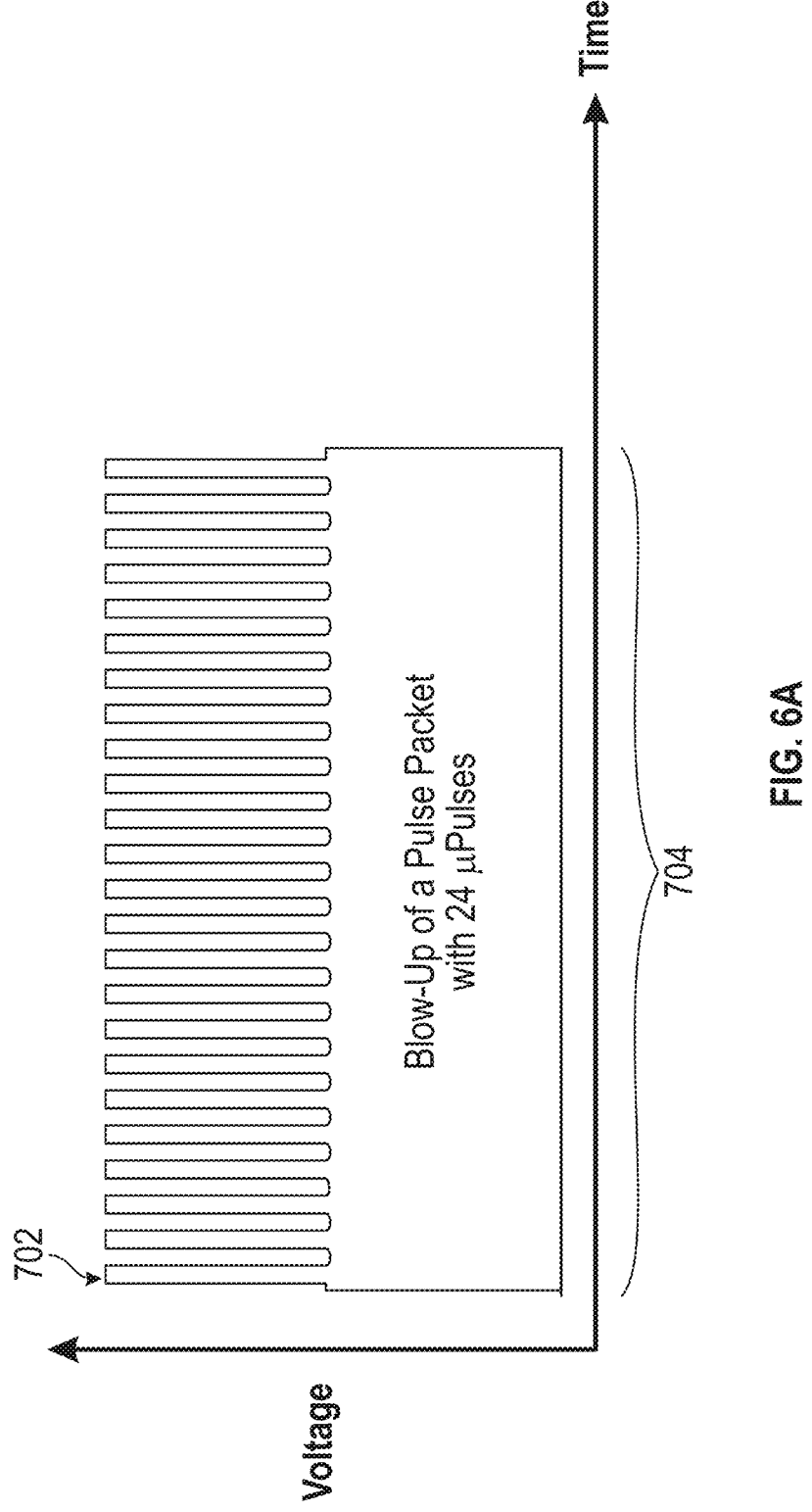
FIG. 6A illustrates an expanded view of an example packet comprising a plurality of sub-pulses delivered in rapid succession, according to some embodiments.
Figure 6B:
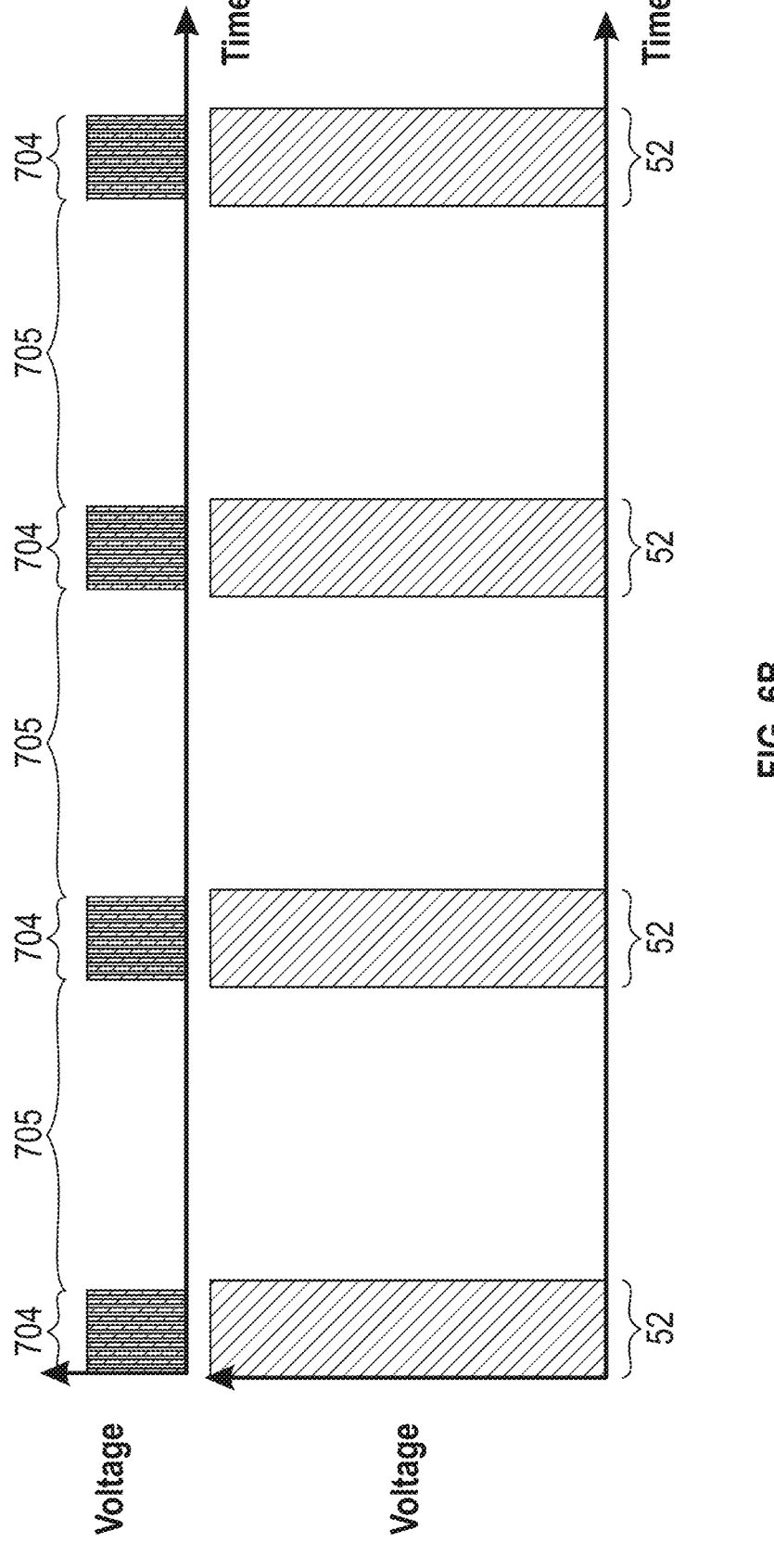
FIG. 6B illustrates exemplary graphs of a plurality of sub-pulses (top) and non-burst pulses (bottom), according to some embodiments.

In some embodiments, the electrodes in the catheter may be activated using at least one packet (also referred to as a burst pulse, operating in burst mode operation) comprising a plurality of sub-pulses. FIGS. 6A and 6B illustrate exemplary graphs of a plurality of sub-pulses (top) and non-burst pulses (bottom), according to some embodiments. The duration of a sub-pulse 702 may be less than the duration of a non-burst pulse 52, as shown in the figure. The sub-pulses 702 within a packet 704 may be delivered in rapid succession (e.g., with a frequency of 100 Hz-10 kHz). The packets 704 may be delivered in bursts. The method of generating a shock wave in a shock wave catheter system comprises applying a plurality of sub-pulses 702 within a packet 704. In some aspects, a sub-pulse 702 generates a shock wave. The time between adjacent sub-pulses 702 (non-active sub-pulse period (time between the end of a sub-pulse and the start of an adjacent sub-pulse)) may be less than the time between adjacent packets 704 (non-active packet period (time between the end of a packet and the start of an adjacent packet)).

The frequency of the sub-pulses 702 within a packet 704 and/or the frequencies of the packets 704, may be determined based on the properties of the calcium and/or tissue being affected by the catheter system. For example, a higher (increased) frequency (of the sub-pulses 702 or of the packets 704) may be used when treating soft materials. Additionally or alternatively, other properties, such as number of sub-pulses 702 within a packet 704, duration of the sub-pulses 702, peak power of a sub-pulse 702, electrical pulse amplitude, and/or sonic output may be adjusted when treating soft materials. In some examples, embodiments of the disclosure include varying the frequency of the sub-pulses 702 within a packet 704. Additionally or alternatively, the frequencies of the packets 704 may vary. In some embodiments, the properties of the sub-pulses 702 (e.g., number of sub-pulses 702 within a packet 704, the duration of at least one sub-pulse 702, the peak power of at least one sub-pulse 702, frequency of the sub-pulses 702, electrical pulse amplitude, sonic output, etc.) may be determined based on the properties of the calcium and/or tissue affected (treated) by the catheter system. For example, the properties of the sub-pulses and/or packets may be determined based on the hardness, thickness, acoustic properties (e.g., acoustic impedance), etc. of the calcium/tissue. A controller (e.g., controller 990 of FIG. 9) may be configured to control the properties of the sub-pulses 702.

Figure 7:
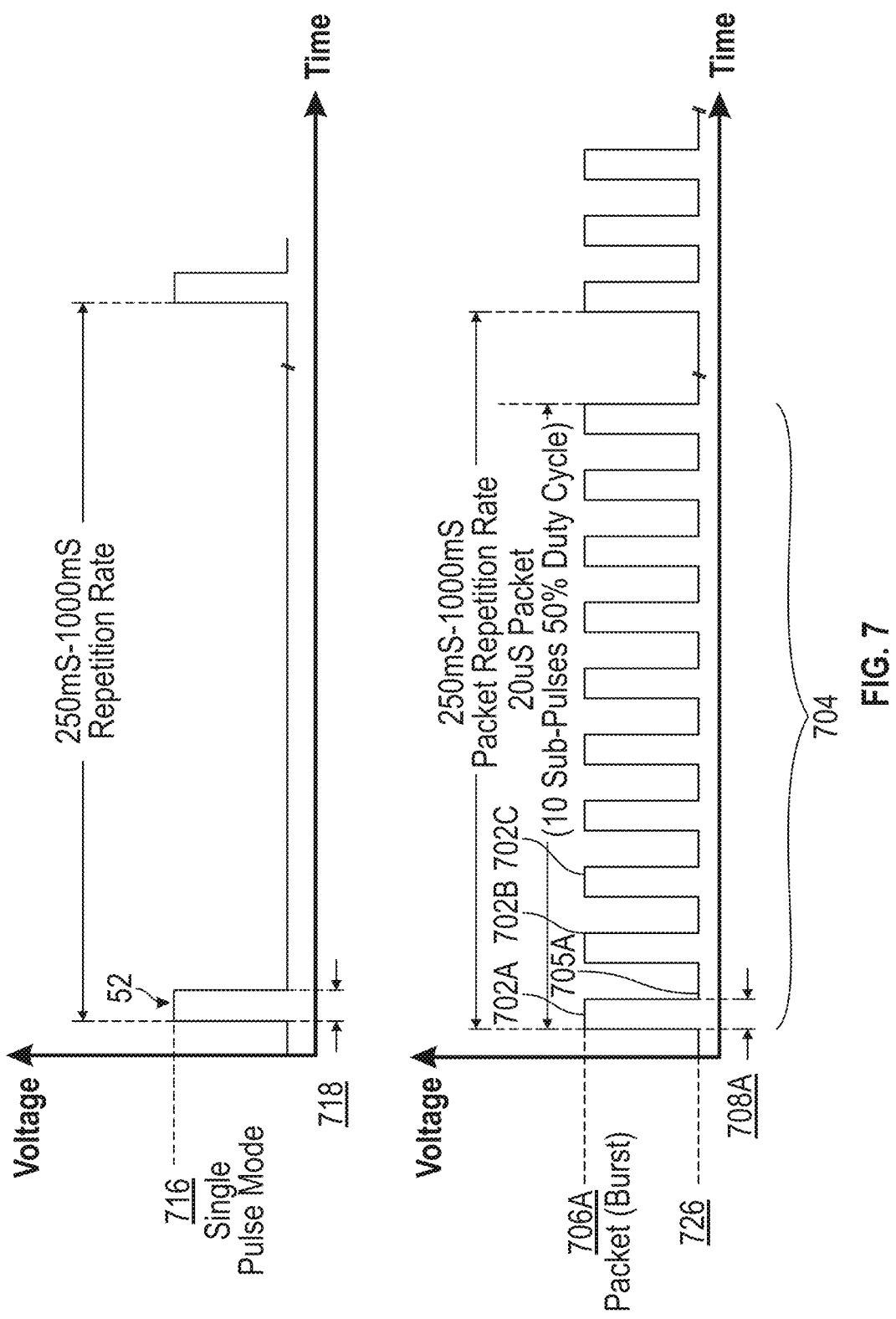
FIG. 7 illustrates an exemplary graph comparing non-burst (non-packet) pulses (top) and a plurality of sub-pulses (bottom), according to some embodiments.

FIG. 7 illustrates an exemplary graph comparing non-burst (non-packet) pulses 52 (top) and a plurality of sub-pulses 702 (bottom), according to some embodiments. The non-burst pulse 52 (top) may comprise a single pulse, having a 1 μs pulse width, that is activated at a repetition rate of 250-1000 mS. The non-burst pulses may have amplitudes as low as 500 volts, or in the range of 1000 volts to 10,000 volts. The energy pulses may be delivered at a slow frequency, e.g., 1-4 Hz.

A packet 704 (bottom) may comprise a plurality of sub-pulses 702. In some embodiments, a sub-pulse 702 may have a duration (pulse width) of 1 μs or shorter. The packet 704 may have a 20 μs (or longer) duration and a 50% duty cycle, for example. In some embodiments, a packet 704 comprises 10 sub-pulses 702. In some embodiments, a packet 704 may be activated at a repetition rate of 250-1000 mS (non-active packet period). A first sub-pulse 702A may break up a first amount of calcium, and additional sub-pulses 702B, 702C, etc. may break up the calcium even more.

A packet 704 may comprise a plurality of sub-pulses 702 delivered in rapid succession. For example, a packet 704 may comprise 24 sub-pulses 702. In some embodiments, the packets 704 may have a frequency similar to pulse 52 (e.g., frequency of 1-4 Hz). In some embodiments, the frequency of the sub-pulses 702 may be at least 100 times more than the frequency of the pulse 52 or packet 704.

Figure 8A:
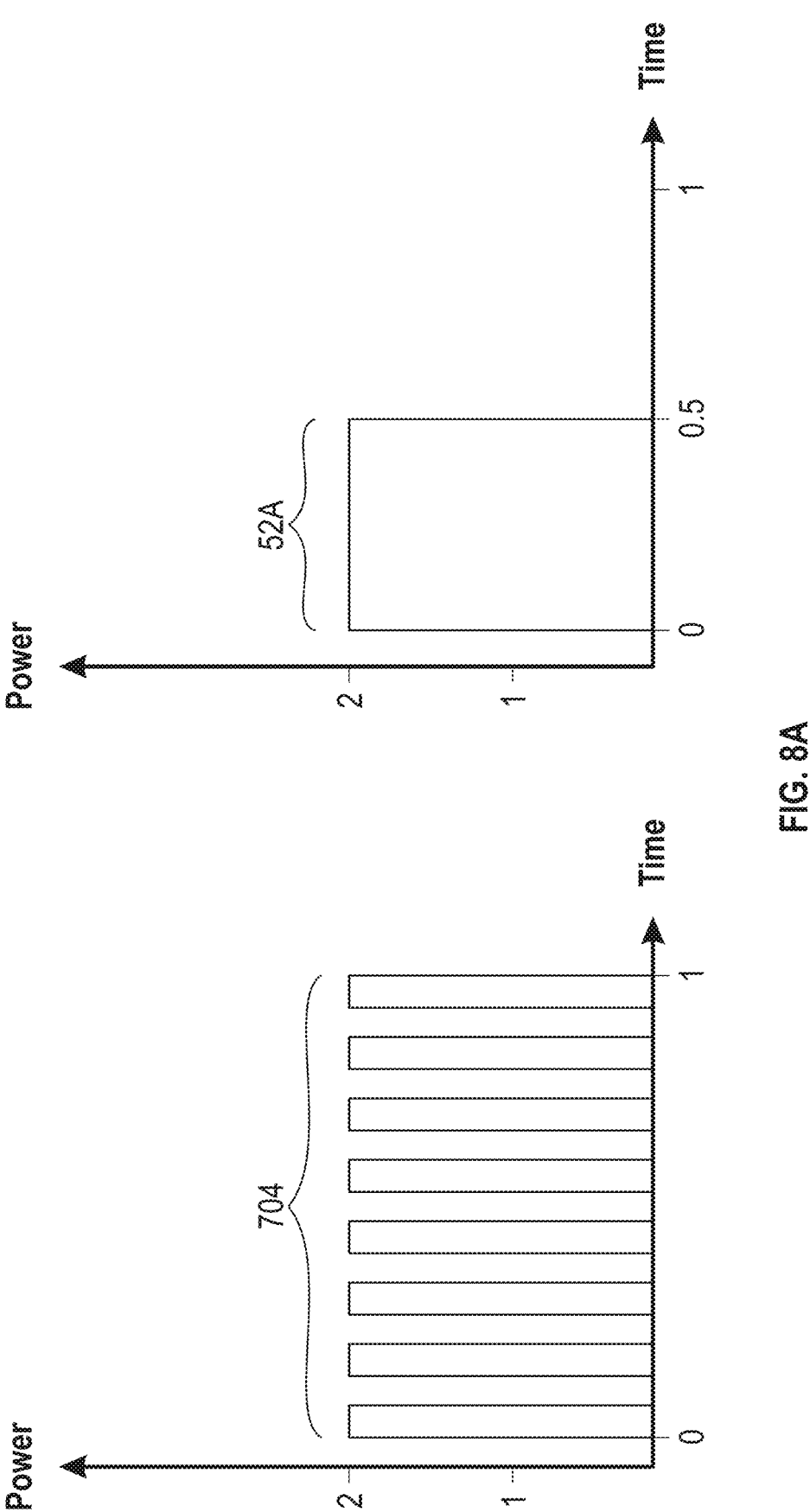
FIG. 8A illustrates an example comparison of power and energy (area under the power vs. time curve) for a packet comprising sub-pulses and a non-burst pulse, according to some embodiments.

The peak power of a sub-pulse 702 may be higher but its energy may be less compared to the peak power and energy of a non-burst pulse 52. As a result, less energy is required for a sub-pulse 702 than a non-burst pulse 52 for a given amount of average power. FIG. 8A illustrates an example comparison of power and energy (area under the power vs. time curve) for a packet 704 comprising sub-pulses 702 and a non-burst pulse 52A. As shown in the figure, the sub-pulses 702 of the packet 704 may comprise the same peak power as the non-burst pulse 52A. For a given amount of time (e.g., 0.5 seconds), the energy delivered for the packet 704 may be less (e.g., half) than the energy delivered for the non-burst pulse 52A. For the same amount of energy delivered, a greater amount of time may be required to deliver a packet 704 of sub-pulses 702 than to deliver a non-burst pulse 52A.

Figure 8B:
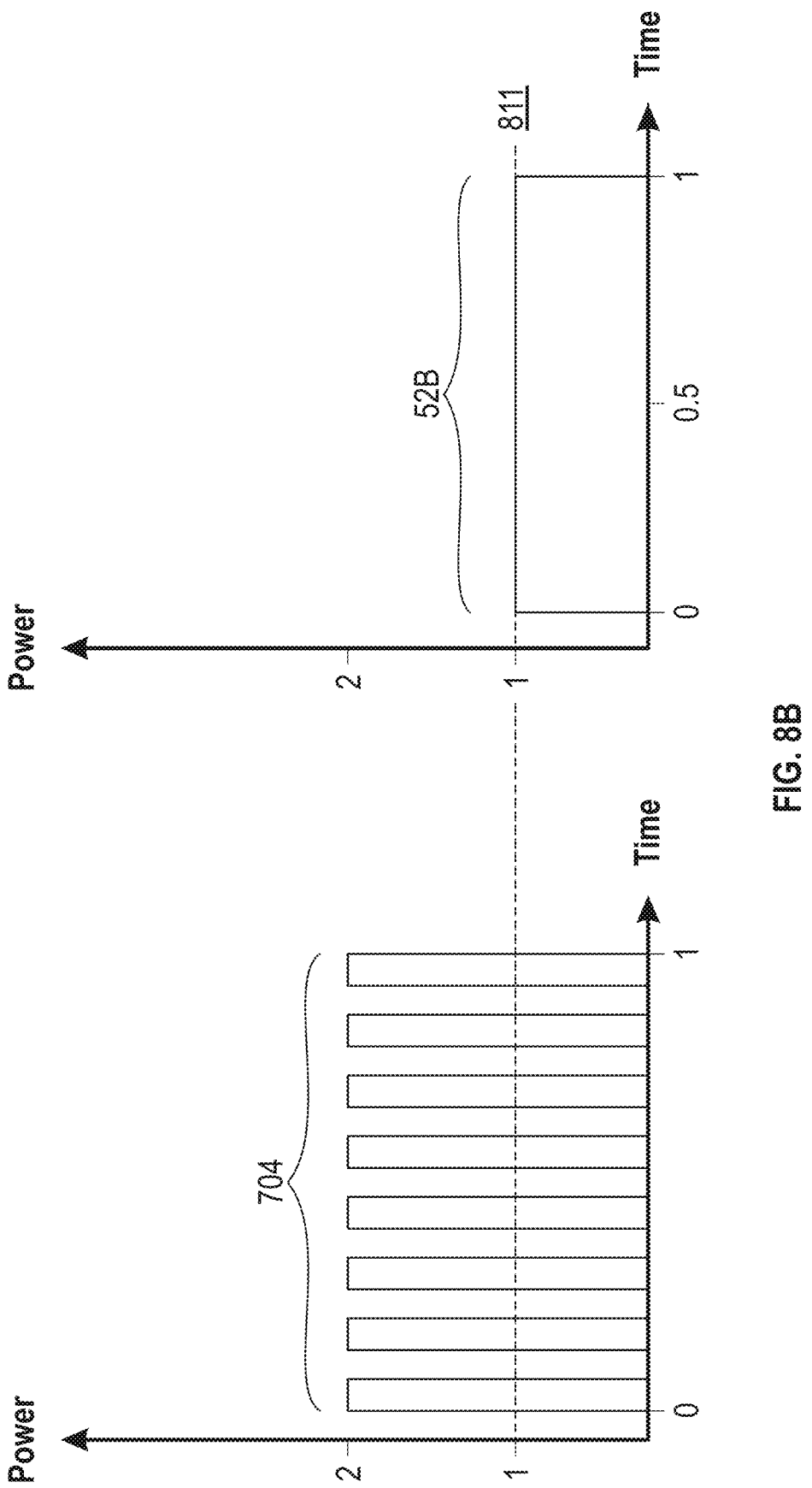
FIG. 8B illustrates an example comparison of power and energy for a packet comprising sub-pulses and a non-burst pulse, according to some embodiments.

FIG. 8B illustrates an example comparison of power and energy for a packet 704 comprising sub-pulses 702 and a non-burst pulse 52B. As shown in the figure, the sub-pulses of the packet 704 may comprise a higher peak power compared to the peak power 811 of the non-burst pulse 52B, where the same energy may be delivered in the same amount of time.

Referring back to FIG. 7, sub-pulse 702A may have a peak power 706A and duration 708A. The duration 708A may be shorter than the duration 718 of a non-burst pulse 52. In some embodiments, the average power of the sub-pulses 702 in a packet 704 may be substantially the same as the average power of a non-burst pulse 52. The time between adjacent sub-pulses (e.g., sub-pulse 702A and 702B) may be referred to as the non-active sub-pulse period 705A. During the non-active sub-pulse period, the power may be reduced to a non-active sub-pulse power level 726. One or more non-active sub-pulse voltages may be applied. In some embodiments, the system may not apply one or more voltages during the non-active sub-pulse period. The non-active sub-pulse power level 726 may be less than the peak power 706A; for example, the non-active sub-pulse power level 726 may be 30%, 40%, 50%, etc. (including a non-active power level of 0 Watts) of the peak power 706A. The peak power 706A may be higher than the peak power 716 of a non-burst pulse 52. In some embodiments, the peak power 706A of a sub-pulse 702A may be 250 kW or higher.

The higher peak power 706 of the sub-pulse 702 may result in an electrical arc forming across the electrodes 22 and 24 faster, which may result in a bubble being generated faster. The bursts of sub-pulses 702 with shorter pulse duration 708 may have the same energy, but delivered in a shorter amount of time (e.g., within the duration of a packet 704), leading to faster and more effective therapy. In some instances, the higher frequency (e.g., 100 Hz-10 kHz) of the sub-pulses 702 may also lead to more effective therapy, particularly when treating soft materials, such as soft tissue.

Examples of the disclosure include a shock wave catheter system configured to operate in burst mode operation and non-burst mode operation. The catheter system can be capable of switching between burst mode operation and non-burst mode operation. In some aspects, in burst mode operation, a plurality of sub-pulses, e.g., having a frequency of 100 Hz-10 kHz, duration of 1 μs or shorter, peak power of at least 250 kW or a combination thereof, within a packet are delivered in rapid succession. In some aspects, in non-burst mode operation, packets, e.g., having a frequency of 1-4 Hz, duration longer than 20 μs, peak power of less than 250 kW, or a combination thereof, are delivered. The catheter system may include a user control input that allows a user to select the mode of operation. For example, the user may select the burst mode operation when treating a first material, and then switch to the non-burst mode operation when treating a second material. The first material may be different from the second material, in some examples, such as the first material being softer tissue than the second material. In this manner, the catheter system may be able to deliver more effective therapy by selectively targeting different types of tissues using different operations.

Figure 9:
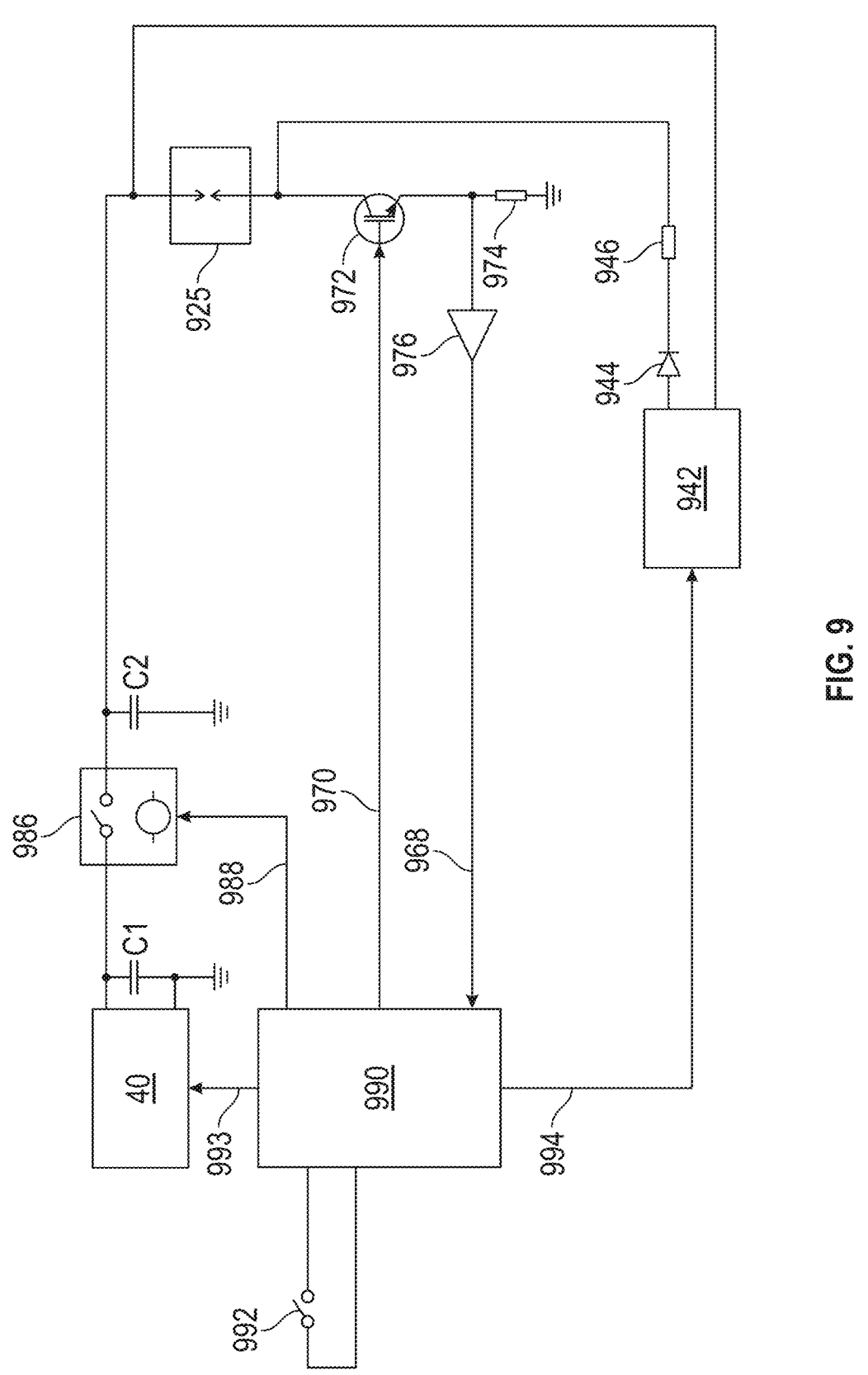
FIG. 9 illustrates a schematic diagram of an example dual stage generator circuit, according to some embodiments.

Embodiments of the disclosure include burst mode operation using a multiple stage generator circuit. FIG. 9 illustrates a schematic diagram of a circuit for burst mode operation of an IVL catheter, according to some embodiments. The circuit comprises a sub-pulse capacitor C2, a reservoir capacitor C1, and a source 40. Capacitor C1 may be a reservoir capacitor that stores energy for a packet 704 (burst energy delivery), and capacitor C2 may be a sub-pulse capacitor that stores and delivers energy for one or more sub-pulses 702. In some aspects, the capacitance of the reservoir capacitor C1 may be greater than the capacitance of the sub-pulse capacitor C2 (e.g., the capacitance of C1 may be more than twice the capacitance of C2). The source 40 can charge the capacitor C1, electrically coupled to the source 40. The sub-pulse capacitor C2 may be configured to store and deliver energy for one or more (e.g., each) sub-pulses 702. An electrode of the emitter 925 is coupled to the capacitor C1, and an electrode of the emitter 925 is coupled to the transistor 972. The source 942 provides a low voltage to the emitter 925 when coupled via transistor 972. The energy of the sub-pulses 702 may be delivered across an emitter 925 (the region of an electrode assembly where the current transmits across the electrode pair 25) for generating a shock wave. The circuit includes a transistor 972 that may couple an electrode 24 of the emitter 925 to a sense resistor 974 based on the pulse signal 970. The resistance of the resistor 974 may limit the charge current for charging the capacitor C1. Coupling the electrode 24 to the sense resistor 974 (e.g., when the pulse signal 970 is high) may lead to a voltage drop across the electrodes 22 and 24 for pulse generation. Applying a high voltage to the electrode pair 25 may cause an electrical current to transmit across the spark gap of the catheter 20.

In some embodiments, operation of the circuit may comprise a plurality of operation modes, including sub-pulse mode and charge mode. In some embodiments, the catheter may operate in sub-pulse mode and charge mode at different times. In sub-pulse mode, energy from the sub-pulse capacitor C2 is transferred to the emitter 925. In charge mode, the reservoir capacitor C1 charges the sub-pulse capacitor C2. The multi-stage generator circuit comprises a switch 986 that is open during sub-pulse mode, electrically decoupling the reservoir capacitor C1 from the emitter 925 so that the source 40 can charge the reservoir capacitor C1.

The switch 986 may be opened or closed depending on the operation mode. During sub-pulse mode, the switch 986 may be open, and the emitter 925 may be electrically coupled to the sub-pulse capacitor C2 and the source 942.

During charge mode, the switch 986 may be closed, electrically coupling the source 40 to the sub-pulse capacitor C2. The transistor 972 may be open during charge mode, thereby allowing source 40 to charge the sub-pulse capacitor C2.

The inclusion of a reservoir capacitor C1 and a sub-pulse capacitor C2 helps reduce the amount of decrease in peak power for subsequent sub-pulses 702 within a packet. The reservoir capacitor C1 is configured to provide energy to the sub-pulse capacitor C2 during charge mode to help maximize the amount of energy stored on the sub-pulse capacitor C2 before the beginning of a sub-pulse 702, thereby allowing the energy delivered to the emitter 925 (during sub-pulse mode) to be close to or the same as the maximum energy storage capabilities of the sub-pulse capacitor C2 for more than one sub-pulse 702.

The sense resistor 974 may be a current sense resistor coupled to a sense amplifier 976. The sense amplifier 976 may generate a sense signal 968 when the current flowing through the electrodes 22 and 24 of the emitter 925 reaches a predetermined current limit (e.g., 10-100 amps). The sense signal 968 may be a current signal sent to the controller 990 when a pulse has been detected. In some embodiments, the sense resistor 974 may control the flow of current, limiting the maximum peak output current. For example, the sense resistor 974 may be a ballast resistor that changes its resistance based on the flow of current.

The reservoir capacitor C1 may be configured to store energy, e.g., for burst energy delivery, when the demands require more energy than stored in sub-pulse capacitor C2 and/or delivery of energy from the source 40 alone is not fast enough for energy delivery during a given sub-pulse 702. The source 40 may be coupled to a reservoir capacitor C1 for charging the reservoir capacitor C1. The reservoir capacitor C1 may also be coupled to ground. A switch 986 selectively couples the reservoir capacitor C1 to the sub-pulse capacitor C2 to transfer the energy stored in the reservoir capacitor C1 to the sub-pulse capacitor C2 and/or the emitter 925. The controller 990 controls the switch 986 using a charge signal 988 such that the switch 986 is closed when charging the sub-pulse capacitor C2 (charge mode). In some embodiments, the switch 986 is closed prior to each sub-pulse 702.

A controller 990 (e.g., microprocessor, a microcontroller, a field programmable gate array (FPGA), etc.), or other similar control circuitry (such as a gate array), controls the overall operation of the catheter system. The controller 990 may receive a button signal coupled to a switch 992. In some embodiments, the button signal may be generated based on a user control input (e.g., a momentary button press) to control the delivery of the sub-pulses 702 and/or packets 704. For example, a high voltage may be delivered to electrode pair 25 when the button signal is high (has a value greater than or equal to a threshold value), closing the switch. The button signal may be high due to, e.g., a user (physician, operator, etc.) pressing a button on the catheter system. In some embodiments, the high voltage may be delivered for a pre-determined duration (e.g., the duration of a packet 704, the duration 708 of a sub-pulse 702, etc.). In some embodiments, the high voltage may be delivered for a duration based on the duration of the button press. The controller 990 may stop delivery of the high voltage when the HV control signal 993 is low, for example. The HV control signal 993 may be low (has a value less than a threshold value) when the pre-determined duration has elapsed, when the physician or operator is no longer pressing the button to the catheter system.

The circuit 900 comprises a source 942 that may be a low voltage power supply (LVPS). The source 942 may be used to bias the emitter 925 to generate one or more gas bubbles, e.g., in a fluid surrounding the electrode 22, electrode 24, or both. In some embodiments, the source 942 may keep the current flowing through the emitter 925 low between adjacent sub-pulses 702 (the non-active sub-pulse period 705A within a packet 704, when a non-active sub-pulse power level 726 is being applied to the electrode pair 25). The source 942 may be coupled to a diode 944 that prevents the pulse current flowing through the source 942 and a resistor 946 that limits the current from the source 942. The source 942 may provide a low voltage based on a LV control signal 994 from the controller 990.

FIG. 10 illustrates an exemplary flow chart for burst mode operation of an IVL, according to some embodiments. At step 1002, the catheter system is in an initial state. In some embodiments, in the initial state, a physician or operator is not pressing a button, as indicated by the button signal to the controller 990. The switch 986 is open, preventing the reservoir capacitor C1 from discharging stored charge (transferring energy to the sub-pulse capacitor C2 and/or emitter 925). The transistor 972, operating in accordance with the pulse signal 970, does not electrically couple the emitter 925 to the sense resistor 974. The HV control signal 993 from the controller 990 to the source 40 indicates that the source 40 should not be providing power (e.g., the HV control signal 993 is low), and the LV control signal 994 from the controller 990 to the source 942 indicates that the source 942 should not be providing power (e.g., the LV control signal 994 is low). No energy is provided to the electrode pair of the emitter 925.

At step 1004, the catheter system may receive a button signal indicative of a button press from a physician or an operator. In some embodiments, the button signal may be high when the physician or operator is pressing a button on the catheter system and low when the physician or operator is not pressing a button. At step 1006, the source 942 may apply a low voltage to the emitter 925, and at step 1008, the catheter system may wait a time period for a bubble to generate. In some embodiments, the source 942 may apply a low voltage to the electrode 22 and electrode 24 of the emitter 925 in response to the controller 990 sending a corresponding LV control signal 994 (e.g., the LV control signal 994 is high).

At step 1010, the controller 990 may send an HV control signal 993 that causes the source 40 to output a high power. For example, the HV control signal 993 may be high. The source 40 may provide a high power to charge the reservoir capacitor C1.

The controller 990 may then close the switch 986 by using the charge signal 988. Closing the switch 986 after the reservoir capacitor C1 has been charged may cause the sub-pulse capacitor C2 to charge (step 1012). The controller 990 opens the switch 986 to stop charging the sub-pulse capacitor C2.

At step 1014, the energy stored in the sub-pulse capacitor C2 is applied to the emitter 925. This stored energy may be applied via the pulse signal 970 from the controller 990 causing the transistor 972 to electrically couple the electrode 24 of emitter 925 to the sense resistor 974. The power is applied to the emitter 925 for the duration of a sub-pulse 702.

When there is a certain amount of current from the emitter 925 through the transistor 972 through the sense amplifier 976, a sense signal 968 is output to the controller 990. The controller 990 outputs the pulse signal 970 that causes the transistor 972 to electrically decouple the emitter 925 and the sense resistor 974. This electrical decoupling between the emitter 925 and the sense resistor 974 stops energy from being applied to the emitter 925, returning to a non-active sub-pulse power level (step 1016).

At step 1018, a determination is made whether all of the sub-pulses 702 of the packet 704 have been executed. If yes, then the catheter system waits for a non-active packet period (step 1020). If no, then the catheter system repeats steps 1006 to 1016 for the next sub-pulse 702.

Figure 11:
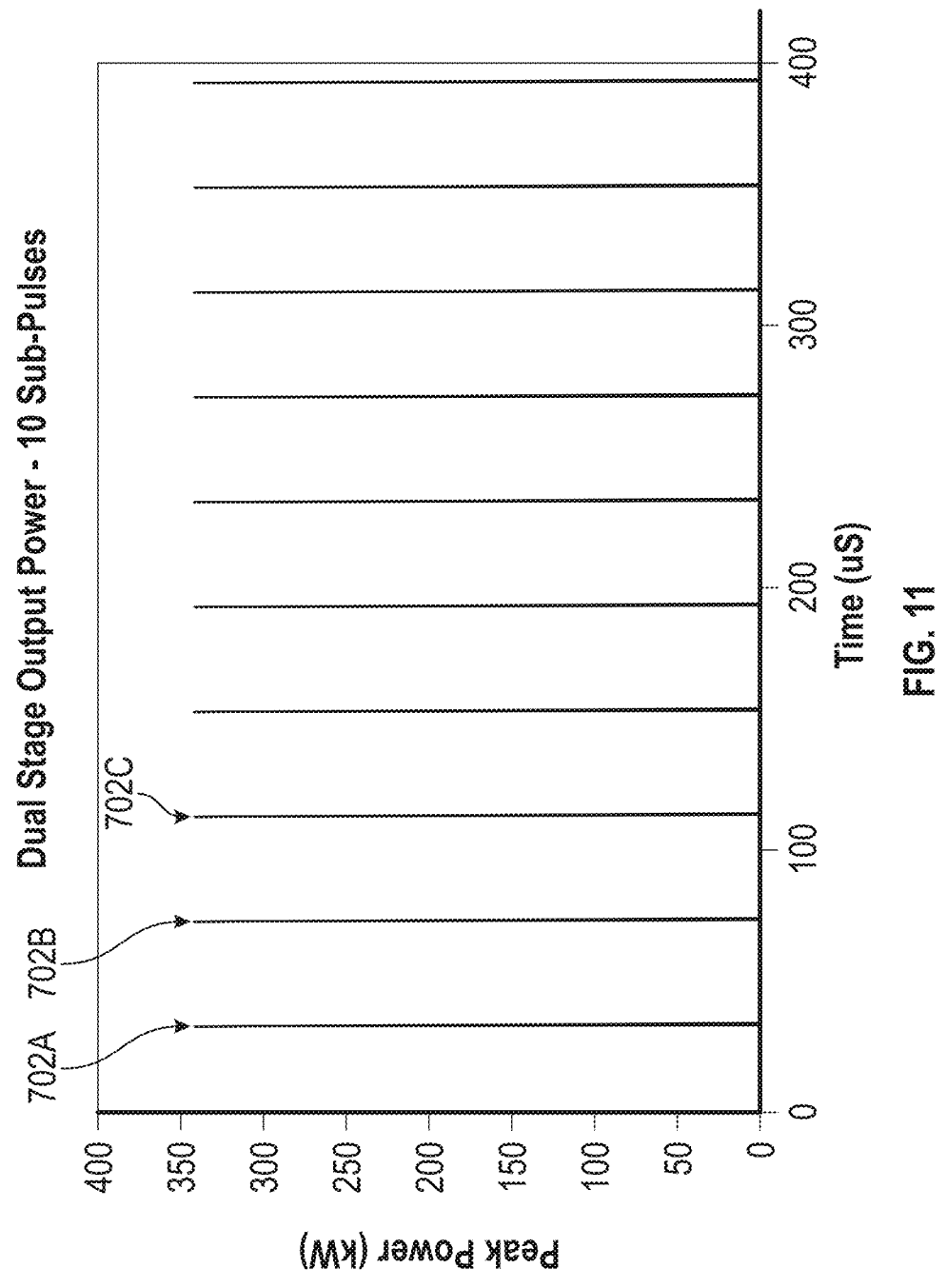
FIG. 11 illustrates a graph of an exemplary burst mode operation of a multi-stage generator circuit for a packet, according to some embodiments.

FIG. 11 illustrates a graph of an exemplary burst mode operation of a multi-stage generator circuit for a packet, according to some embodiments. The multi-stage generator circuit may be more effective at breaking up calcium than the single-stage generator circuit. Although FIG. 11 illustrates a packet 704 as comprising 10 sub-pulses 702, embodiments of the disclosure may include any number of sub-pulses 702 within a packet 704.

The sub-pulses 702 in a packet 704 may have substantially the same peak power. For example, the first sub-pulse 702A may have a peak power of about 340 kW, the second sub-pulse 702B may have a peak power of about 340 kW, the third sub-pulse 702C may have a peak power of about 340 kW, etc.

Figure 12:
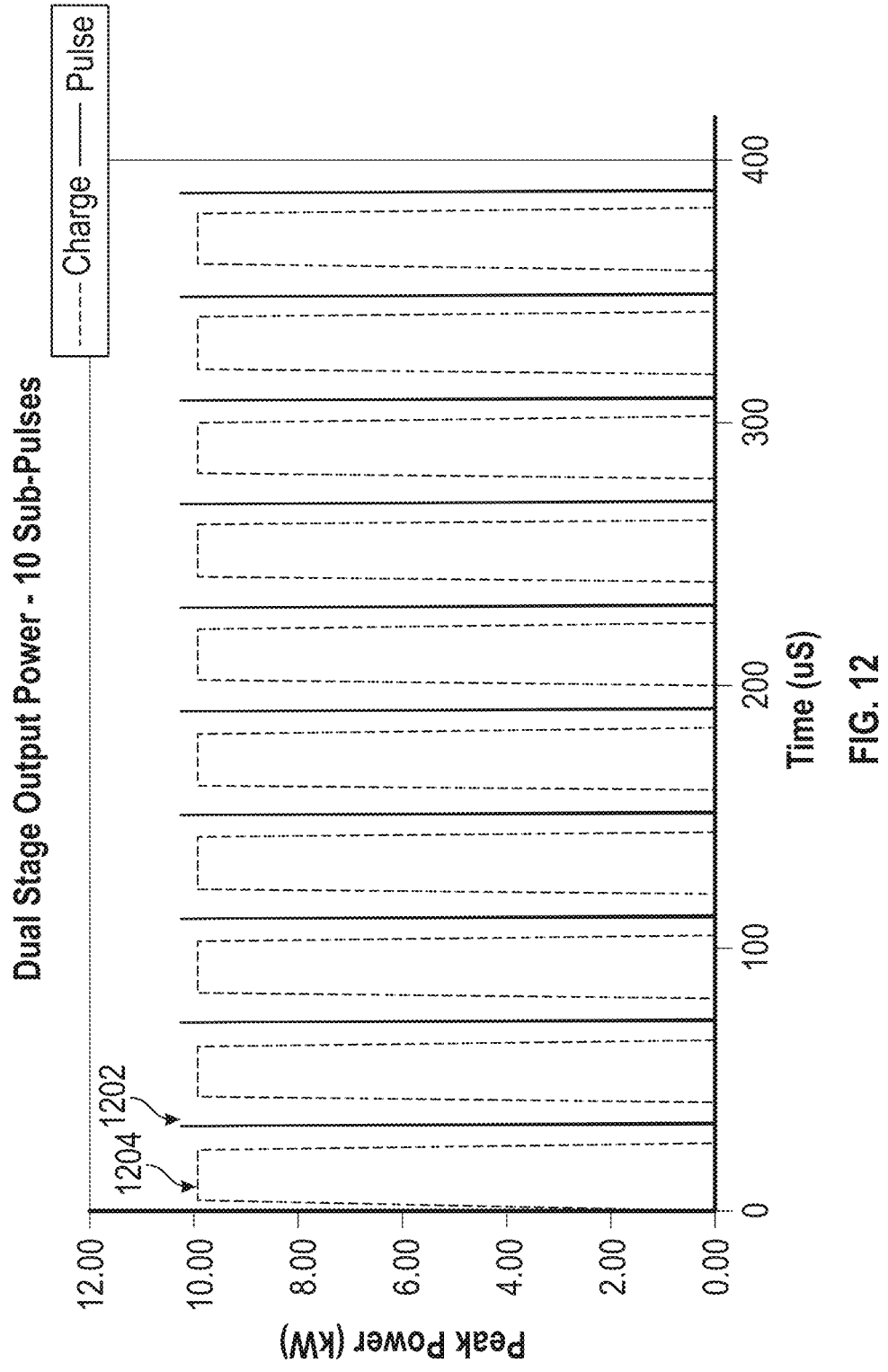
FIG. 12 illustrates a graph of exemplary charge and sub-pulse modes, according to some embodiments.
Figure 13:
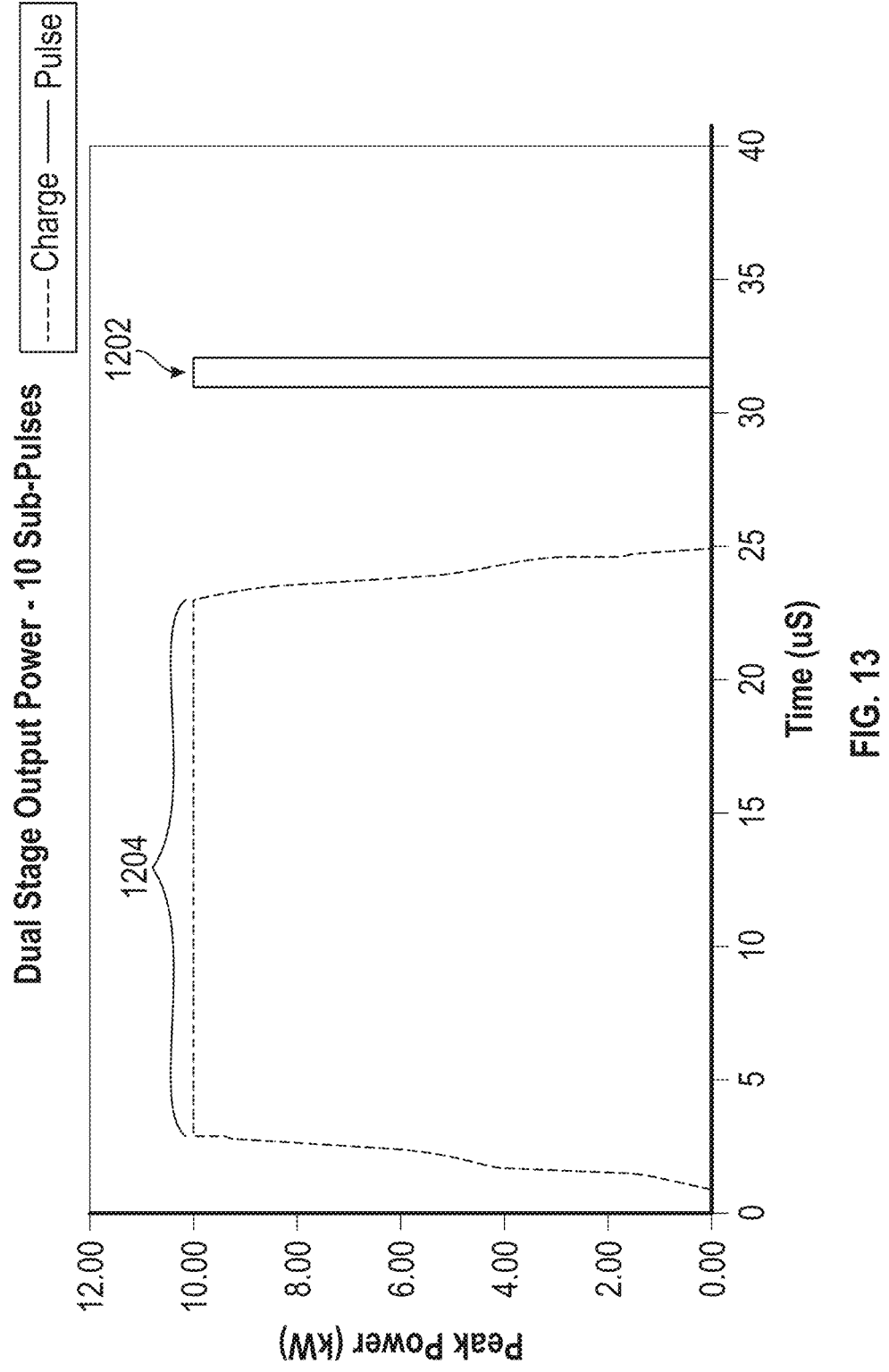
FIG. 13 illustrates an exemplary sub-pulse, according to some embodiments.

FIG. 12 illustrates a graph of exemplary charge and sub-pulse modes, and FIG. 13 illustrates an exemplary sub-pulse, according to some embodiments. The multi-stage generator circuit may be operated in a plurality of operation modes, such as charge mode 1204 and sub-pulse mode 1202. During charge mode 1204, transistor 972 (of FIG. 9) may be open, and the source 942 (of FIG. 9) may apply a low voltage to the emitter 925 (of FIG. 9). The switch 986 (of FIG. 9) being open, allows the source 40 (of FIG. 9) to charge the reservoir capacitor C1.

During sub-pulse mode 1202, the switch 986 (of FIG. 9) closes momentarily to charge the sub-pulse capacitor C2. After the sub-pulse capacitor C2 charges, the switch 986 is open, allowing the sub-pulse capacitor C2 to provide energy to the emitter 925 (of FIG. 9).

As shown in the single sub-pulse of FIG. 13, the circuit may operate in charge mode 1204 and sub-pulse mode 1202 at different times. In some embodiments, the duration of the charge mode 1204 may be greater than the duration of the sub-pulse mode 1202.

Figure 14:
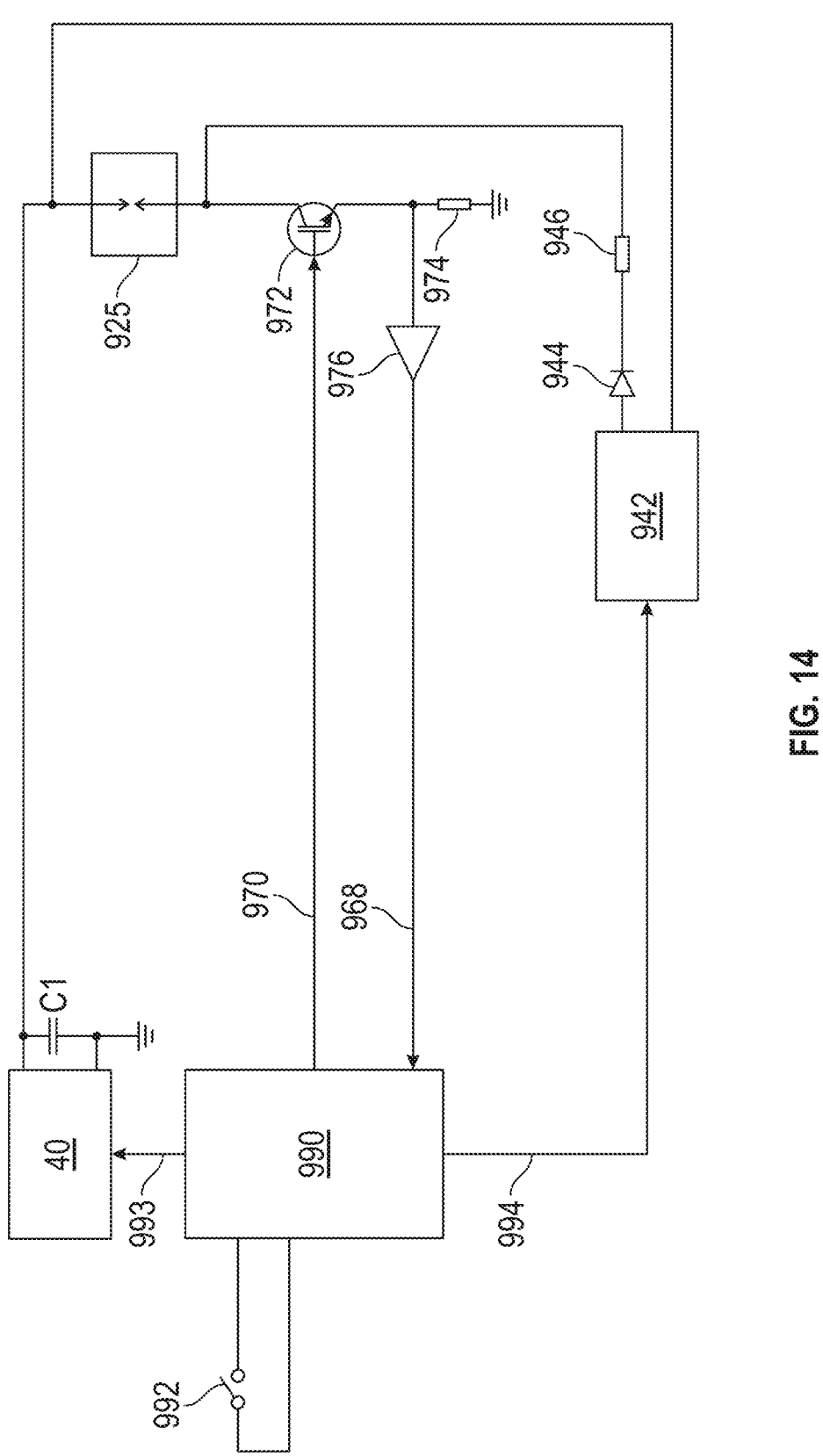
FIG. 14 illustrates a simplified schematic diagram of an example single-stage generator circuit, according to some embodiments.

Embodiments of the disclosure include burst mode operation using a single-stage generator circuit. FIG. 14 illustrates a simplified schematic diagram simulating an example single-stage generator circuit, according to some embodiments. A multi-stage generator circuit may comprise additional transistors and capacitors compared to the single-stage generator circuit. For example, the single-stage generator circuit may not comprise switch 986 or sub-pulse capacitor C2.

Figure 15:
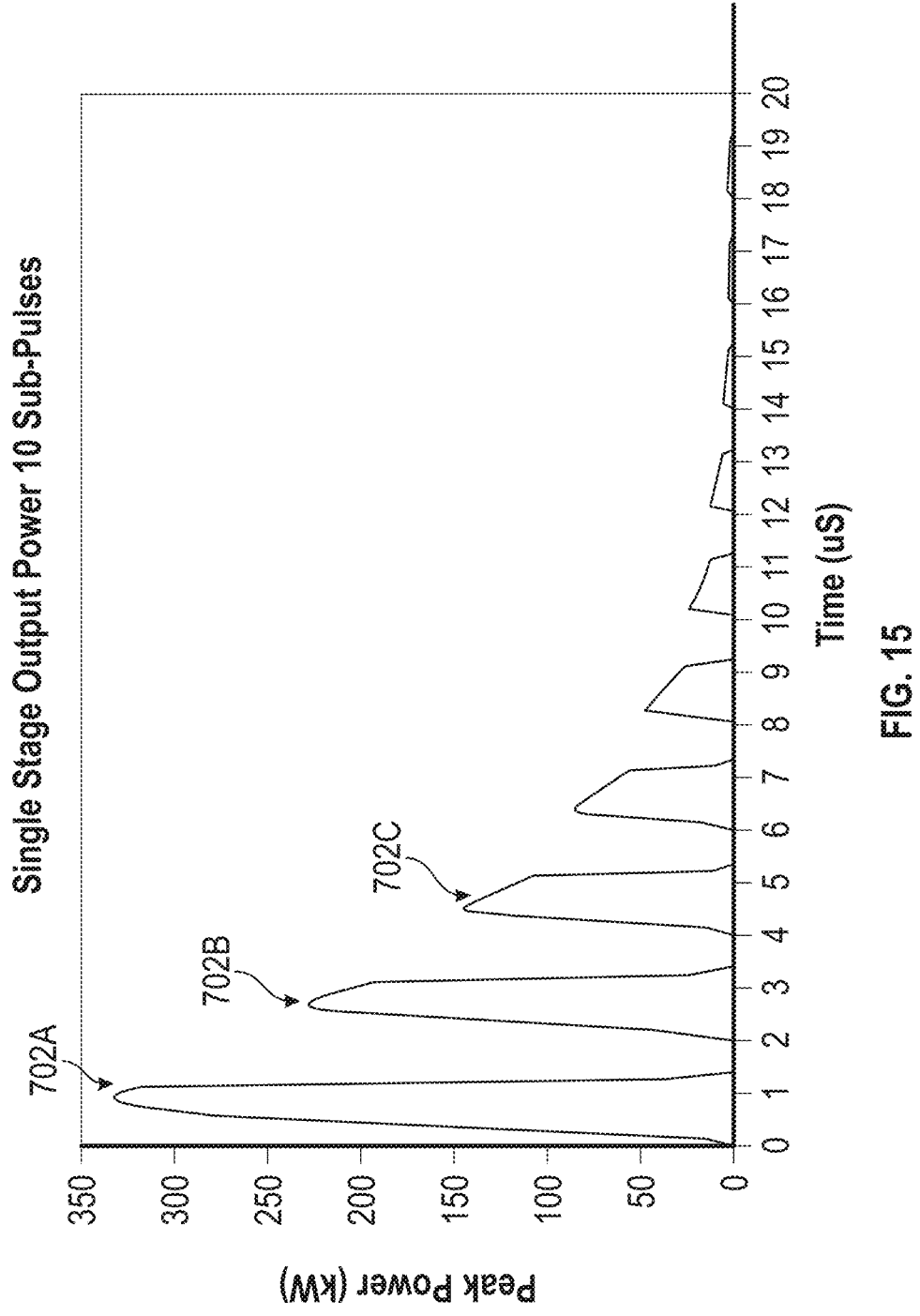
FIG. 15 illustrates a graph of an exemplary burst mode operation of a single-stage generator circuit for a packet, according to some embodiments.
Figure 16:
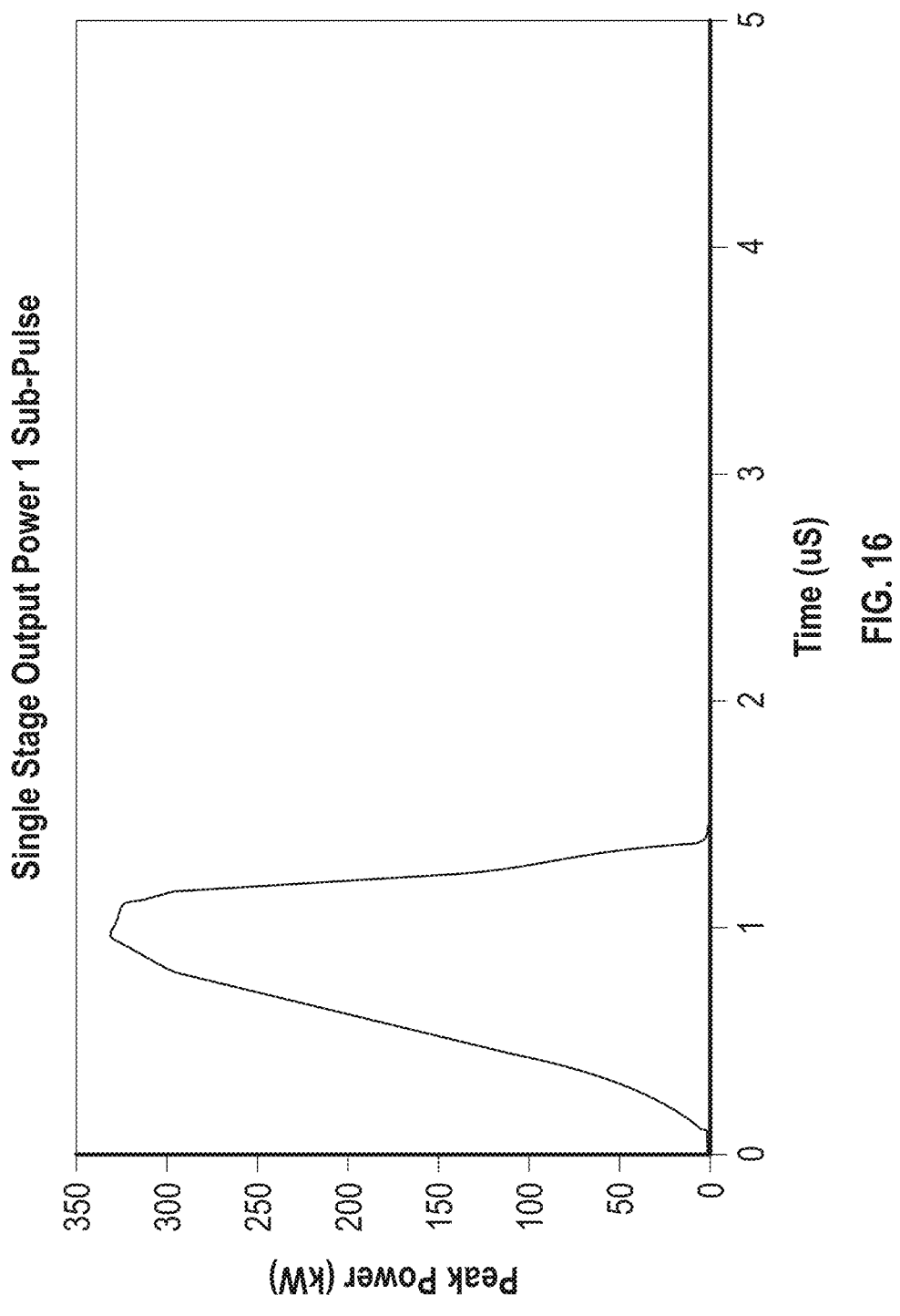
FIG. 16 illustrates an exemplary sub-pulse, according to some embodiments.

FIG. 15 illustrates a graph of an exemplary burst mode operation of a single-stage generator circuit for a packet, and FIG. 16 illustrates an exemplary sub-pulse, according to some embodiments. Although FIG. 15 illustrates a packet 704 as comprising 10 sub-pulses 702, embodiments of the disclosure may include any number of sub-pulses 702 within a packet 704, including greater than or equal to 10 sub-pulses.

Within a packet 704, the first sub-pulse 702A may have the highest peak power, and then the peak power(s) of subsequent sub-pulse(s) decrease. The amount of energy stored in the capacitor C1 (of FIG. 14) is reduced for each sub-pulse due to energy being transferred to emitter 925. For example, the first sub-pulse 702A may have a peak power of about 340 kW (also shown in FIG. 15), the second sub-pulse 702B may have a peak power of about 220 kW (the peak power of the second sub-pulse 702B may be less than the peak power of the first sub-pulse 702A), the third sub-pulse 702C may have a peak power of about 150 kW (the peak power of the third sub-pulse 702C may be less than the peak power of the second sub-pulse 702B), etc. In some embodiments, the peak power may exhibit an exponential decay over time and/or for subsequent sub-pulses 702 within a packet 704, as shown in FIG. 15.

Operation of the single-stage generator circuit may be similar to the operation shown in FIG. 10. In some embodiments, the operation of the single-stage generator may not include steps related to charging capacitors, such as charging the reservoir capacitor of step 1010 and charging the sub-pulse capacitor of step 1012.

In some embodiments, the multi-stage generator circuit may be operated as a single stage or two stages. For example, the capacitor C1 (of FIG. 14) may be initially charged at the beginning of a packet 704. Once the capacitor C1 is charged, the transistor Q1 may be configured to be open during the remainder of the packet 704.

Although shock wave devices described herein generate shock waves based on high voltage applied to electrodes, it should be understood that a shock wave device additionally or alternatively may comprise a laser and optical fibers as a shock wave emitter system whereby the laser source delivers energy through an optical fiber and into a fluid to form shock waves and/or cavitation bubbles.

The electrode assemblies and catheter devices described herein may be used for treating coronary occlusions, such as lesions in vasculature, and a variety of other occlusions, such as occlusions in the peripheral vasculature (e.g., above-the-knee, below-the-knee, iliac, carotid, etc.). For further examples, similar designs may be used for treating soft tissues, such as cancer and tumors (i.e., non-thermal ablation methods), blood clots, fibroids, cysts, organs, scar and fibrotic tissue removal, or other tissue destruction and removal. Electrode assembly and catheter designs could also be used for neurostimulation treatments, targeted drug delivery, treatments of tumors in body lumens (e.g., tumors in blood vessels, the esophagus, intestines, stomach, or vagina), wound treatment, non-surgical removal and destruction of tissue, or used in place of thermal treatments or cauterization for venous insufficiency and fallopian ligation (i.e., for permanent female contraception).

In one or more examples, the electrode assemblies and catheters described herein could also be used for tissue engineering methods, for instance, for mechanical tissue decellularization to create a bioactive scaffold in which new cells (e.g., exogenous or endogenous cells) can replace the old cells; introducing porosity to a site to improve cellular retention, cellular infiltration/migration, and diffusion of nutrients and signaling molecules to promote angiogenesis, cellular proliferation, and tissue regeneration similar to cell replacement therapy. Such tissue engineering methods may be useful for treating ischemic heart disease, fibrotic liver, fibrotic bowel, and traumatic spinal cord injury (SCI). For instance, for the treatment of spinal cord injury, the devices and assemblies described herein could facilitate the removal of scarred spinal cord tissue, which acts like a barrier for neuronal reconnection, before the injection of an anti-inflammatory hydrogel loaded with lentivirus to genetically engineer the spinal cord neurons to regenerate.

Figure 17:
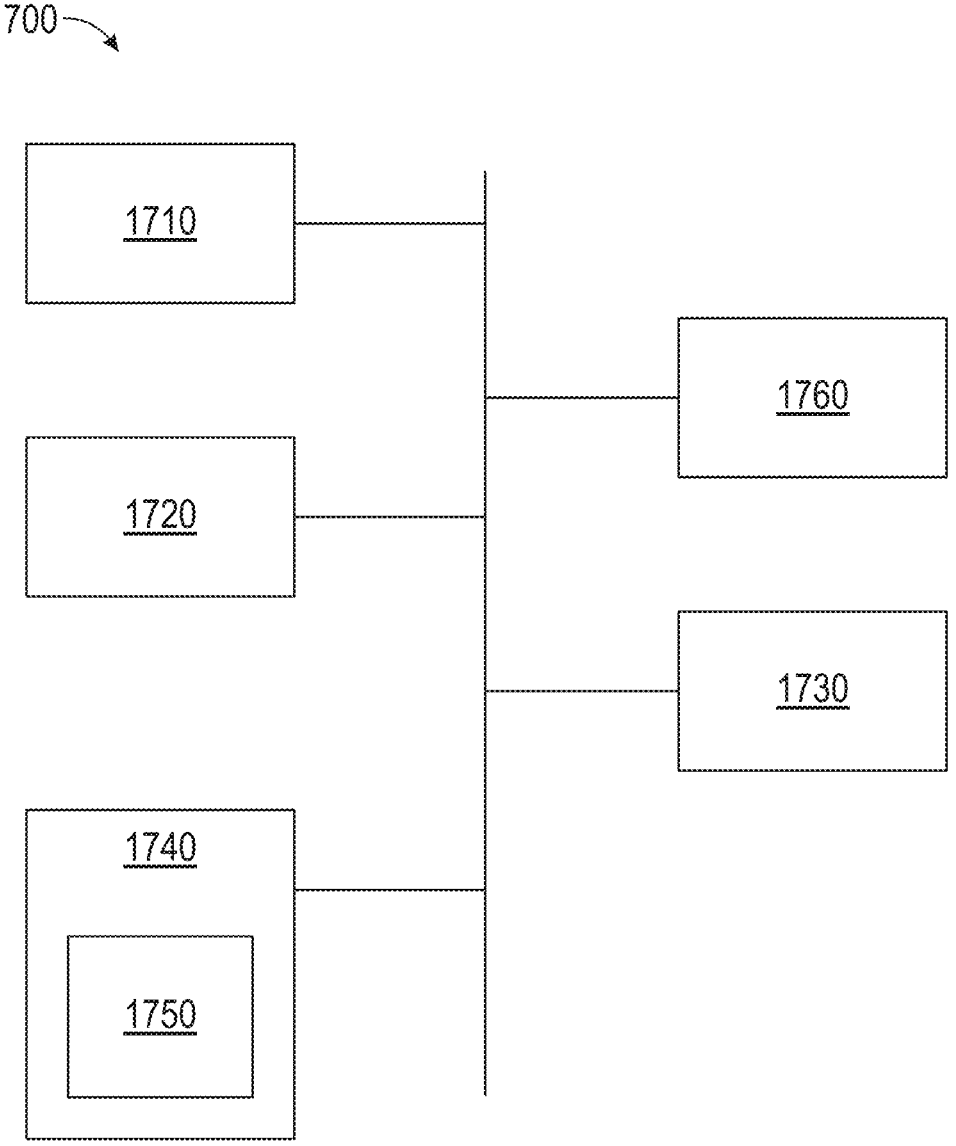
FIG. 17 illustrates an exemplary of a computing system, according to some embodiments.

FIG. 17 illustrates an exemplary of a computing system 1700, in accordance with some examples of the disclosure. System 1700 can be a client or a server. As shown in FIG. 17, system 1700 can be any suitable type of processor-based system, such as a personal computer, workstation, server, handheld computing device (portable electronic device) such as a phone or tablet, or dedicated device. The system 1700 can include, for example, one or more of input device 1720, output device 1730, one or more processors 1710, storage 1740, and communication device 1760. Input device 1720 and output device 1730 can generally correspond to those described above and can either be connectable or integrated with the computer.

Input device 1720 can be any suitable device that provides input, such as a push-button switch, a touch screen, keyboard or keypad, mouse, gesture recognition component of a virtual/augmented reality system, or voice-recognition device. Output device 1730 can be or include any suitable device that provides output, such as a display, touch screen, haptics device, virtual/augmented reality display, or speaker.

Storage 1740 can be any suitable device that provides storage, such as an electrical, magnetic, or optical memory including a RAM, cache, hard drive, removable storage disk, or other non-transitory computer readable medium. Communication device 1760 can include any suitable device capable of transmitting and receiving signals over a network, such as a network interface chip or device. The components of the computing system 1700 can be connected in any suitable manner, such as via a physical bus or wirelessly.

Processor(s) 1710 can be any suitable processor or combination of processors, including any of, or any combination of, a central processing unit (CPU), graphics processing unit (GPU), field programmable gate array (FPGA), programmable system on chip (PSOC), and application-specific integrated circuit (ASIC). Software 1750, which can be stored in storage 1740 and executed by one or more processors 1710, can include, for example, the programming that embodies the functionality or portions of the functionality of the present disclosure (e.g., as embodied in the devices as described above)

Software 1750 can also be stored and/or transported within any non-transitory computer-readable storage medium for use by or in connection with an instruction execution system, apparatus, or device, such as those described above, that can fetch instructions associated with the software from the instruction execution system, apparatus, or device and execute the instructions. In the context of this disclosure, a computer-readable storage medium can be any medium, such as storage 1740, that can contain or store programming for use by or in connection with an instruction execution system, apparatus, or device.

Software 1750 can also be propagated within any transport medium for use by or in connection with an instruction execution system, apparatus, or device, such as those described above, that can fetch instructions associated with the software from the instruction execution system, apparatus, or device and execute the instructions. In the context of this disclosure, a transport medium can be any medium that can communicate, propagate or transport programming for use by or in connection with an instruction execution system, apparatus, or device. The transport computer readable medium can include, but is not limited to, an electronic, magnetic, optical, electromagnetic, or infrared wired or wireless propagation medium.

System 1700 may be connected to a network, which can be any suitable type of interconnected communication system. The network can implement any suitable communications protocol and can be secured by any suitable security protocol. The network can comprise network links of any suitable arrangement that can implement the transmission and reception of network signals, such as wireless network connections, T1 or T3 lines, cable networks, DSL, or telephone lines.

System 1700 can implement any operating system suitable for operating on the network. Software 1750 can be written in any suitable programming language, such as C, C++, Java, or Python. In various embodiments, application software embodying the functionality of the present disclosure can be deployed in different configurations, such as in a client/server arrangement or through a Web browser as a Web-based application or Web service, for example.

The elements and features of the exemplary electrode assemblies and catheters discussed above may be rearranged, recombined, and modified, without departing from the present invention. Furthermore, numerical designators such as "first," "second," "third," "fourth," etc. are merely descriptive and do not indicate a relative order, location, or identity of elements or features described by the designators. For instance, a "first" shock wave may be immediately succeeded by a "third" shock wave, which is then succeeded by a "second" shock wave. As another example, a "third" emitter may be used to generate a "first" shock wave and vice versa. Accordingly, numerical designators of various elements and features are not intended to limit the disclosure and may be modified and interchanged without departing from the subject invention.

As provided herein, it should be appreciated that any disclosure of a numerical range describing dimensions or measurements such as thicknesses, length, weight, time, frequency, temperature, voltage, current, angle, etc. is inclusive of any numerical increment or gradient within the ranges set forth relative to the given dimension or measurement.

It should be noted that the elements and features of the example catheters illustrated throughout this specification and drawings may be rearranged, recombined, and modified without departing from the present invention. For instance, while this specification and drawings describe and illustrate catheters having several example balloon designs, the present disclosure is intended to include catheters having a variety of balloon configurations. The number, placement, and spacing of the electrode pairs of the shock wave generators can be modified without departing from the subject invention. Further, the number, placement, and spacing of balloons of catheters can be modified without departing from the subject invention.

It should be understood that the foregoing is only illustrative of the principles of the invention, and that various modifications, alterations and combinations can be made by those skilled in the art without departing from the scope and spirit of the invention. Any of the variations of the various catheters disclosed herein can include features described by any other catheters or combination of catheters herein. Furthermore, any of the methods can be used with any of the catheters disclosed. Accordingly, it is not intended that the invention be limited, except as by the appended claims.

The invention claimed is:

1. A method performed by a catheter system, comprising:
operating an energy source in a first mode, wherein operating the energy source in the first mode includes:
applying, by the energy source, a first packet of energy to an electrode pair configured to produce cavitation waves within a catheter, the first packet of energy including consecutive sub-pulses having a first peak power and separated by a first duration; and
applying, by the energy source, a second packet of energy to the electrode pair so that the first packet of energy and the second packet of energy are separated by a second duration longer than the first duration, the second packet of energy including consecutive sub-pulses having a second peak power and separated by the first duration; and
operating the energy source in a second mode, wherein operating the energy source in the second mode includes:
applying, by the energy source, a series of pulses to the electrode pair so that consecutive pulses in the series of pulses are separated by a third duration longer than the first duration, each of the pulses in the series of pulses having a third peak power lower than the first peak power and the second peak power.

2. The method of claim 1, wherein the cavitation waves are produced by the electrode pair in response to the consecutive sub-pulses in each of the first packet of energy and the second packet of energy.

3. The method of claim 1, further comprising:
applying, by the energy source, a voltage to the electrode pair, the voltage producing a cavitation bubble in a conductive medium surrounding the electrode pair.

4. The method of claim 3, wherein the conductive medium comprises a liquid.

5. The method of claim 1, wherein the consecutive sub-pulses have the same voltage in at least one of the first packet of energy or the second packet of energy.

6. The method of claim 1, wherein the consecutive sub-pulses have different voltages in at least one of the first packet of energy or the second packet of energy.

7. The method of claim 1, wherein each of the pulses in the series has a longer pulse duration than any of the consecutive sub-pulses in the first packet of energy or the second packet of energy.

8. The method of claim 1, further comprising:
receiving user input indicating a selection of the first mode or the second mode; and
switching between the first mode and the second mode responsive to the user input.

9. The method of claim 1, wherein at least one sub-pulse of the consecutive sub-pulses included in the first packet of energy or the second packet of energy generates a cavitation wave.

10. The method of claim 1, wherein the energy source is configured to operate in the first mode or the second mode based on a tissue type associated with a target.

11. The method of claim 10, further comprising:
receiving an input indicating the tissue type associated with the target; and
configuring the energy source to operate in the first mode when the input indicates that the tissue type is a first type; or
configuring the energy source to operate in the second mode when the input indicates that the tissue type is a second type, the first type being softer than the second type.

12. The method of claim 1, wherein the cavitation waves are configured for treating a calcified lesion in a vasculature.

13. The method of claim 1, wherein the cavitation waves are configured for treating a kidney stone in a urinary system.

14. The method of claim 1, wherein the applying of the first and second packets of energy to the electrode pair comprises:

discharging a first capacitor across the electrode pair to produce the consecutive sub-pulses in the first packet of energy and the consecutive sub-pulses in the second packet of energy; and transferring energy from a second capacitor to the first capacitor between the consecutive sub-pulses so that the consecutive sub-pulses maintain substantially the same peak power.

15. A catheter system comprising:

a catheter including an electrode pair configured to produce cavitation waves;

an energy source; and a controller configured to:

operate the energy source in a first mode, wherein operating the energy source in the first mode includes:

applying, by the energy source, a first packet of energy to the electrode pair, the first packet of energy including consecutive sub-pulses having a first peak power and separated by a first duration; and applying, by the energy source, a second packet of energy to the electrode pair based on the energy source so that the first packet of energy and the second packet of energy are separated by a second duration longer than the first duration, the second packet of energy including consecutive sub-pulses having a second peak power and separated by the first duration; and operating the energy source in a second mode, wherein operating the energy source in the second mode includes:

applying, by the energy source, a series of pulses to the electrode pair so that consecutive pulses in the series of pulses are separated by a third duration longer than the first duration, each of the pulses in the series of pulses having a third peak power lower than the first peak power and the second peak power.

16. The catheter system of claim 15, wherein the energy source comprises a voltage generator, a current generator, or a pulse generator.

17. The catheter system of claim 15, further comprising:

a first capacitor configured to store and deliver energy from the energy source for each of the consecutive sub-pulses of the first and second packets of energy; and a second capacitor configured to transfer energy from the energy source to the first capacitor within the first duration.

18. The catheter system of claim 15, wherein the controller is further configured to:

apply a voltage to the electrode pair based on the energy source, the voltage producing a cavitation bubble in a conductive medium surrounding the electrode pair.

19. A controller for a catheter system comprising:

one or more processors; and a memory storing instructions that, when executed by the one or more processors, cause the controller to:

operate an energy source in a first mode, wherein operating the energy source in the first mode includes:

applying, by the energy source, a first packet of energy to an electrode pair configured to produce cavitation waves within a catheter, the first packet of energy including consecutive sub-pulses having a first peak power and separated by a first duration; and applying, by the energy source, a second packet of energy to the electrode pair so that the first packet of energy and the second packet of energy are separated by a second duration longer than the first duration, the second packet of energy including consecutive sub-pulses having a second peak power and separated by the first duration; and operating the energy source in a second mode, wherein operating the energy source in the second mode includes:

applying, by the energy source, a series of pulses to the electrode pair so that consecutive pulses in the series of pulses are separated by a third duration longer than the first duration, each of the pulses in the series of pulses having a third peak power lower than the first peak power and the second peak power.

* * * * *